United States Patent [19]
Herrlich et al.

[11] Patent Number: 5,885,575
[45] Date of Patent: Mar. 23, 1999

[54] ANTIBODIES THAT REACT WITH VARIANT CD44 SURFACE PROTEINS

[75] Inventors: Peter Herrlich, Karlsruhe; Helmut Ponta, Linkenheim, both of Germany; Ursula Guenthert, Basel, Switzerland; Siegfried Matzku, Wiesenbach; Achim Wenzel, Heidelberg, both of Germany

[73] Assignees: Kernforschungszentrum Karlsruhe GmbH; Universitaet Karlsruhe, both of Karlsruhe; Deutsches Krebsforschungszentrum, Heidelberg, Germany

[21] Appl. No.: 478,882

[22] Filed: Jun. 7, 1995

Related U.S. Application Data

[62] Division of Ser. No. 946,497, Nov. 9, 1992, Pat. No. 5,506,119.

[30] Foreign Application Priority Data

May 7, 1990 [DE] Germany .......................... 40 14 510.7
Mar. 30, 1991 [WO] WIPO ...................... PCT/EP91/00614

[51] Int. Cl.⁶ ........................ A61K 39/395; G01N 33/58; C12P 21/08; C07K 16/30
[52] U.S. Cl. .................................. 424/139.1; 424/143.1; 435/7.23; 435/70.21; 435/331; 435/334; 435/344.1; 435/346; 530/387.9; 530/388.85; 530/389.7; 530/391.3
[58] Field of Search ............................ 530/387.9, 388.22, 530/388.85, 389.7, 391.1, 391.3; 435/7.1, 7.5, 7.2, 7.23, 7.24, 331, 334, 344.1, 7.92, 70.21, 346; 424/139.1, 143.1

[56] References Cited

PUBLICATIONS

Seaver, S. Genetic Engineering News, vol. 14, pp. 10, 14, Aug. 14, 1994.
The Dictionary of Immunology, Herber, W. J. et al. (Eds.), Academic Press, New York, NY., 1995.
Volume 1: Immunochemistry, Edited by Weir, D. M. et al., Blackwell Scientific Publications, Boston, MA, Chapter 14 and pp. 38.5–38.6, 1986.
Birnbaum et al., Anticancer Research 8: 1185–1191 (1988).
Matzku et al., Cancer Research 49: 1294–1299 (Mar. 1, 1989).
Lehmann et al., Proc. Natl. Acad. Sci. USA 86: 9891–9895 (1985).
Chan et al., Science 251: 1600–1602 (1991).
Maniatis et al., Molecular Cloning, pp. 382–389 (1982).
Kugelman et al., J. Invest. Dermotol. 99:381–385 (1992).
Bowie et al., Science 247: 1306–1310 (1990).
Kumar et al., Proc. Natl. Acad. Sci. 87: 1337–1341 (1990).
Ellis, Vaccines, Plotkin & Mortiner Eds., W. B. Saunders Co., pp. 568–575 (1988).
Young et al., Proc. Natl. Acad. Sci. 80:1194–1198 (1983).

*Primary Examiner*—Frank C. Eisenschenk
*Assistant Examiner*—Evelyn Rabin
*Attorney, Agent, or Firm*—Foley & Lardner

[57] ABSTRACT

The inventon relates to antibodies that react with a variant epilope in the extracellular region of a variant CD44 polypeptide, wherein the variant epitope has the amino acid sequence:
I S S T I S T T P R A P D H T K Q N Q D W T Q W N P S H S N P E
V L L Q T T T R M T D V D R N G T T A Y E G N W N P E A H P P L
I H H E H H E E E E T P H S T S T I O A T P S S T T E E T A T Q
K E Q W F G N R W H E G Y R Q T P R E D S H S T T G T A A A S A
H T S H P M Q G R T T P S P E D S S W T D F F N P I S H P M G R
G H Q A G R R (residues 53–219 of SEQ ID NO:4).
Methods of using the antibodies to identify variant epitopes also are provided.

12 Claims, 19 Drawing Sheets

FIG. 2

| FIG. 2a | FIG. 2b |
|---------|---------|
| FIG. 2c | FIG. 2d |
| FIG. 2e | FIG. 2f |
| FIG. 2g | FIG. 2h |

FIG. 3a

| FIG. 3a-1 | FIG. 3a-2 |
|-----------|-----------|
| FIG. 3a-3 | FIG. 3a-4 |

FIG. 3b

| FIG. 3b-1 |
|-----------|
| FIG. 3b-2 |
| FIG. 3b-3 |

FIG. 2a

1      CTCATTGCCCAGCAGCCCCAGCCAGTGACAGGTTCCATTCACCCTCTTTGC

113    ATGGACAAGGTTTGGTGGCACACAGCTTGGGGACTACTTTGCCTCTTACAGTTGAGCCTG
       M   D   K   V   W   W   H   T   A   W   G   L   L   L   L   Q   L   S   L

233    AAAAATGGCCGCTACAGTATCTCCAGGACTGAAGCAGCCTCTGCCGAGGCTTTCAAC
       K   N   G   R   Y   S   I   S   R   T   E   A   A   D   L   C   E   A   F   N

353    AGGTATGGGTTCATAGAAGGACACGTGGTAATCCCGAGGATCCACCCCAACGCTATCTGT
       R   Y   G   F   I   E   G   H   V   V   I   P   R   I   H   P   N   A   I   C

473    TATTGCTTCAATGCCTCAGCTCCTCTTGAAGAAGACTGTACATCAGTCACAGACCTACCC
       Y   C   F   N   A   S   A   P   L   E   E   D   C   T   S   V   T   D   L   P

593    AAGAAGGGCGAGTATAGAACACACCAAGAAGACATCGATGCCTCAAACATTATAGATGAG
       K   K   G   E   Y   R   T   H   Q   E   D   I   D   A   S   N   I   I   D   E

FIG. 2b

```
CCCTTCCCCCGGCGACCCCTTTTCCAGAGGCTACTAGATCCTTTGGTTTCATCCTGCACATC

GCACAGCAGCAGATCGATTTGAATATAACCTGCCGTTACCCAGGTGTATTCCATGTGGAG
 A  Q  Q  I  D  L  N  I  T  C  R  Y  A  G  V  F  H  V  E

ACCACCTTGCCCACCATGGCTCAGATGGAGTTAGCCCTGAGAAAGGGTTTGAAACATGC
 T  T  L  P  T  M  A  Q  M  E  L  A  L  R  K  G  F  E  T  C

GCAGCCAACAACACAGGAGTGTATATCCTCCTCGCATCCAACACCTCCCACTATGACACA
 A  A  N  N  T  G  V  Y  I  L  L  A  S  N  T  S  H  Y  D  T

AATTCCTTCGATGGACCAGTTACCATAACTATTGTCAACCGTGATGGCACCCGCTACAGC
 N  S  F  D  G  P  V  T  I  T  I  V  N  R  D  G  T  R  Y  S

GATGTCAGCAGTGGATCCACCATTGAGAAGAGCACCCCAGAAGGCTACATTTTGCACACC
 D  V  S  S  G  S  T  I  E  K  S  T  P  E  G  Y  I  L  H  T
```

FIG. 2c

```
 713 GACCTTCCCACTTCACAGCCTACTGGAGACCGGGATGACGCCTTCTTTATTGGGAGCACC
       D  L  P  T  S  Q  P  T  G  D  R  D  D  A  F  F  I  G  S  T

833 ACCCAGTGGAACCCGATCCATTCAAACCCAGAAGTACTACTTCAGACAACCACCAGGATG
       T  Q  W  N  P  I  H  S  N  P  E  V  L  L  Q  T  T  T  R  M

953 CCTCCTTTCAATAACCATGAGTATCAGGATGAAGAGGAGACCCCACATGCTACAAGCACA
       P  P  F  N  N  H  E  Y  Q  D  E  E  E  T  P  H  A  T  S  T

1073 GAGAATGAATGGCAGGGGAAGAACCCACCCCAAGTGAAGACTCCCATGTGACAGAA
       E  N  E  W  Q  G  K  N  P  P  T  P  S  E  D  S  H  V  T  E

1193 GAGGATGTTTCATGGACCGATTTCTTCGACCCAATCTCACATCCAATGGGACAAGGTCAT
       E  D  V  S  W  T  D  F  F  D  P  I  S  H  P  M  G  Q  G  H
```

FIG. 2e

```
1313 GGTCCTGCGGAGGAGACCCTCAGATTCCAGAGTGGCTTATCATCTTGGCATCCCCTGG
      G  P  A  R  R  P  Q  I  P  E  W  L  I  L  A  S  L  L

1433 AAGAAGCTGGTGATCAACAGTGGAACAGTGGAAGACAGGAAACCAAGTGAAC
      K  K  L  V  I  N  S  G  N  G  T  V  E  D  R  K  P  S  E

1553 ACTCCGGACCAGTTTATGACAGCTGATGAGACCCGGAATCTGCAGAGTGTGGATATGA
      T  P  D  Q  F  M  T  A  D  E  T  R  N  L  Q  S  V  D  M

1673 TACTGGGAGCTGGGACCCCTTAACAGATGCAATGTGCTACTGATTATTTTTATTGGGA

1793 AATAGCATTGCTTTCTGAAATGAGGGTCTCTTCCAGTTCCTCCTTAGAGGCCTTGCAT

1913 AGTCCCAGGTAACATCCACCAGCTAAGGATTCCCCAGAACTTAGAGAGAGATTGGTCTC

2033 GCAGTGGATGGGAGATCAGGTGTTACTGGTTACACACTCTCTTTATAGACTCCCTTCTG

2153 GCTATTTATCTTTGTTTTTGAAATATCAAACCCTGGAGGTCCTTTTTCAGTATGACT
```

FIG. 2f

```
CGCTGGCTCTGATTCTTGCCCTCTGCATTGCTGTCAACAGTAGGAGAAGGTGTGGGCAGAAG
 A  L  A  L  I  L  A  V  C  I  A  V  N  S  R  R  R  C  G  Q  K

TCAACGGGGAGGCCAGCAAGTCTCAGGAAATGGTGCATTGGTGAACAAGGAACCAACAGAG
 L  N  G  E  A  S  K  S  Q  E  M  V  H  L  V  N  K  E  P  T  E

AGATTGGGGTGTAGTGCCTATGCCACTAACTTGAAAAGACACAACAATTGGAGACATGTCAT
 K  I  G  V  U

TTATTTGGGCATAAAATTCCCTTTTTTTGTTTTTAAAAGTTTGTTTTCCAATTTATGAA

TACCAGGGTATGCTACCATAGGCTTCTACCAAATGAATACTCTTGGTCCCGATTGAACCCAA

TGGGAGGAAATTTGAATGGGTCCATATGCCCTCCCAGCAGTCCAATCTGTAGGCATTGCTTT

CTGGAAAATTCCACATGCTTCTGAGAGATTCCCCAAAGGTGACGCTATTTATCTTTAGTAA

TTTTTTATTTGTTTTTTATTTGTTTTTTAGGTTACTTTGTCAGAAGCATAACAGGGT
```

FIG. 2g

```
2273  ATAAGTTGATTCATAATAAATACCTGTCCATCTTCCATCTTGACCTGTGTGCTGTGA
2393  GGTCCCTCTGAAACTCATGTTAGAGCATCCGTGCCCTGGGTTACCCAGCTGAAT
2513  TGTTCAAGAATCTGAATTGGGAGTAGGAGAGCTTCTGTCCCTTTATGTTTCGATAAC
2633  GTTTCATAGACACTGATCTTATTGGCACTTTCACAAAACAGTGTGGAGGGACTTCTG
2753  GCATGAGGAGGCATGATGTACAACCCCCAGACCACTCTTTCCATCACCACATTTGTTG
2873  AAGAATGCCCCACCCCTGGAATCTTACCACCAGATGAGCAGGTTTATGGTTTAGCA
2993  CCAGGATGCCCCATTGCTCCTAGGTCTTCCCAGGTACCTTGTAGAAGAACTTAAATCT
3113  TAAATTTATATGTTTAATAGTTTTTTTTTCAAATAAAAACAAACACAAAAAGGAAAAAA
```

FIG. 2h

TCCTTCAGTTTCTAAATCAGCAAGGTCTGAGTCTCTTTGTAGCACATCAATGTGACCTTAGTAT

CTCAGAAGATCAAGGAGACAGGAGCACTGTTTTCATTCTAGGACTATCAAAGGGTTTCTCTCC

CACCCATTTCTCTTCTTAAAGGGCACATTAAGTTTTTATATCTTACAACATTCGCGGTCCT

ACACCCTTATAGTAAAAGGAGAAGCCAACAGAAATGAAAGTGTGGACAGAGAGCAGTAGATTG

ATGCTTTCGCAAGCCAGTTGGTACTTAGAATCAGTTCCCCAGGAATCCTTCAAAAGCCAT

AAAGGAGAATGCTGTCACCCTCTGACCCTCATAGTTTTCACATACTGGGCAAGTGTTCATCTG

ATAAAATAAGGCTTTCTCTAAAATGGAACTTCCTTTCTAAGGCTCCCATTTTTACTGTTGAC

AAAAAAAAAAAAAAAAAAAAAAAAAAAAAAA

FIG. 3a-1

```
716   GTACACCCCCATCCCAGACGAAGACAGTCCCTGATCACCGAC----------AGCA
201    V  H  P  I  P  D  E  D  S  P  H  I  T  D  -  -  -  -  S
205    S  Q  P  T  G  D  R  D  D  A  F  F  I  G  S  T  L  A  T  S

821   GACAGACACCTCAGTTTTCTGGATCAGGCATTGATGATGAAGATTTTATCTCCAGCA
236    D  R  H  L  S  F  S  G  S  G  I  D  D  D  E  D  F  I  S  S
245    D  K  Y  P  N  F  S  G  S  G  I  D  D  D  E  D  F  I  S  S

941   TGGAACCCAAGCCATTCAAATCCGGAAGTGCTACTTCAGACAACCACAAGGATGACTGATG
278    W  N  P  S  H  S  N  P  E  V  L  L  Q  T  T  T  R  M  T  D
285    W  N  P  I  H  S  N  P  E  V  L  L  Q  T  T  T  R  M  T  D

1061  CTCATTCACCATGAGCATCATGAGGAAGAGACCCCACATTCTACAAGCACAATCCAGG
316    L  I  H  H  E  H  H  E  E  E  E  T  P  H  S  T  S  T  I  Q
325    F  N  N  H  E  Y  Q  D  E  E  E  T  P  H  A  T  S  T  T  H

1181  AGATGGCATGAGGATATCGCCAAACACCCAGAGAAGACTCCCATTCGACAACAGGACAG
356    R  W  H  E  G  Y  R  Q  T  P  R  E  D  S  H  S  T  T  G  T
365    E  W  Q  G  K  N  P  P  T  P  S  E  D  S  H  V  T  E  G  T
```

FIG. 3a-2

```
                                                                              ─▶ D I
CAGACAGAATCCCTGCTACCACAGGCTGGGAGCCAAATGAAGAAAATGAAGATGAAAGA                  human
 T  D  R  I  P  A  T  T  G  H  E  P  N  E  E  N  E  D  E  R
 T  E  S  N  T  N  P  T  G  W  K  P  N  E  N  E  D  E  T                    rat ─▶ D II
CCATTTCAACCACCACACCGGGCCCTTTGACCACCACAAAACAGAACCAGGACTGGACCCAG              human
 T  I  S  T  T  P  R  A  F  D  H  T  K  Q  N  Q  D  W  T  Q
 T  I  A  T  T  P  W  V  S  A  H  T  K  Q  N  Q  E  R  T  Q                 rat TAGACAGAAATGGCCACCACTGCTTATGAAGGAAACTGGAACCCAGAAGCACACCCTCCC                human
 V  D  R  N  G  T  T  A  Y  E  G  N  W  N  P  E  A  H  P  P
 I  D  R  N  S  T  S  A  H  G  E  N  H  T  Q  E  P  Q  P  P                 rat
 III CAACTCCTAGTAGTACAACGGAAGAAACAGCTACCCAGAAGGAACAGTGGTTTGGCAAC                 human
 A  T  P  S  S  T  T  E  E  T  A  T  Q  K  E  Q  W  F  G  N
 A  D  P  P  N  S  T  T  E  E  A  A  T  Q  K  E  K  W  F  E  N              rat CTGCAGCCTCAGCTCATACCAGCCATCCAATGCAAGGAAGGACAACACCAAGCCCAGAG                 human
 A  A  S  A  H  T  S  H  P  M  Q  G  R  T  T  P  S  P  E
 -  T  A  S  A  H  N  N  H  P  S  Q  R  M  T  T  Q  S  Q  E                 rat
```

FIG. 3a-3

```
1301  GACAGTCCTGGACTGATTTCTTCAACCCAATCTCACACCCCATGGGACGAGGTCATCAAG
398     D  S  S  H  T  D  F  F  N  P  I  S  H  P  M  G  R  G  H  Q
404     D  V  S  H  T  D  F  F  D  P  I  S  H  P  M  G  Q  G  H  Q

1421  CCAAACACAGGTTTGGTGGAAGATTTGGACAGGACCTCTTTCAATGACAACGCCAGC
438     P  N  T  G  L  V  E  D  L  D  R  T  G  P  L  S  M  T  T  Q
443     P  N  T  H  L  V  E  D  L  N  R  T  G  P  L  S  V  T  T  P
                                                          ↑
                                                        D  V

1541  CCAACAACTTCTACTCTGACATCAAGCAATAGGAATGATGTCACAGGTGGAAGAAGAGACC
476     P  T  T  S  T  L  T  S  S  N  R  N  D  V  T  G  G  R  R  D
483     P  T  T  S  V  L  P  S  S  T  K  -  -  S  G  R  R  R  G

1661  ACGAAGGAAAGCAGGACCTTCATCCCAGTGACCTCAGCTAAGACTGGGTCCTTTGGAGTTA
518     T  K  E  S  R  T  F  I  P  V  T  S  A  K  T  G  S  F  G  V
520     T  M  E  N  G  T  L  F  P  V  T  P  A  K  T  E  V  F  G  E
```

FIG. 3a-4

↱ D IV
CAGGAAGAAGGATGGATATGGACTCCAGTCATAGTACAACGCTTCAGCCTACTGCAAAT    human
A  G  R  R  M  D  M  D  S  S  H  S  T  T  L  Q  P  T  A  N
T  E  S  K  -  D  T  G  S  S  H  S  T  T  L  Q  P  T  A  A    rat AGAGTAATTCTCAGAGCTTCTACATCACATGAAGGCTTGGAAGAAGATAAAGACCAT    human
Q  S  N  S  Q  S  F  S  T  S  H  E  G  L  E  E  D  K  D  H
Q  S  H  S  Q  N  F  S  T  L  P  G  E  L  E  E  G  E  D  II   rat CAAATCATTCTGAAGGCTCAACTACTTACTGAAGGTTATACCCTCTCATTACCCACAC    human
P  N  H  S  E  G  S  T  T  L  E  G  Y  T  S  H  Y  P  H
G  S  L  P  R  D  T  T  T  S  L  E  G  Y  T  P  Q  Y  P  D    rat end of variant domaine ↲

CTGCAGTTACTGTTGGA---GATTCCAACTCTAATGTCAATCGTTCCTTATCAGGAGAC    human
T  A  V  T  V  G  -  D  S  N  S  N  V  N  R  S  L  S  G  D
T  E  G  T  V  A  T  D  S  N  F  N  V  D  G  S  L  P  G  D    rat

FIG. 3b-1

|        | | | | | | | | | | | | | | | | 40/37/39 | | | | | | | | | | | | | | | | 80/77/79 |
|--------|---|---|---|---|---|---|---|---|---|---|---|---|---|---|---|---| rMeta-1   M D K V W H F A W G L L C L Q L S L A Q L D H Q L N H I T C R Y A G V F H V E
hCD44     M D K F W W H A A W G L C C V P L S L A - I D L N I T C R F A G V F H V E
mCD44     M D K F W H A A W G L L C L Q L S L A H Q I D L N V T C R Y A G V F E V E rMeta-1   K N G R Y S I S R T E A A D L C K A F N T T L P T M A Q M E L A L R K G F E T C
hCD44     K N G R Y S I S R T E A A D L C K A F N S T L P T M A Q M E K A L S I G F E T C
mCD44     K N G R Y S I S R T E A A D L C Q A F N S T L P T M D Q M K L A L S K G F E T C rMeta-1   R Y G F I E G H V V I P R I H P N A I C A A N N T G V Y I L L T H I T A S N T S H Y D T
hCD44     R Y G F I E G H V V I P R I H P N S I C A A N N T G V Y I L V - Y N T S Q H Y D T
mCD44     R Y G F I E G N V V I P R I H P N H I C A A N H T G V Y I L V T H V H T S H Y D T rMeta-1   Y C F N A S A P L E E D C T S V T D L P N S F D G P V H T H V N R D G T R Y S
hCD44     Y C F N A S A P P E E D C T S V T D L P N A F D G P I T I H V N R D G T R Y V
mCD44     Y C F N A S A P P E E D C T S V T D L P N S F D G P V T I H V N R D G T R Y S rMeta-1   K K G E Y R T H Q E D I D A S N I E K - S T P E G Y I L H
hCD44     Q K G E Y R T N P E D I H P S N S E R S S T P E G Y I L H
mCD44     K K G E Y R T H Q E D I D A H P S N T E K - S T P E G Y I L H

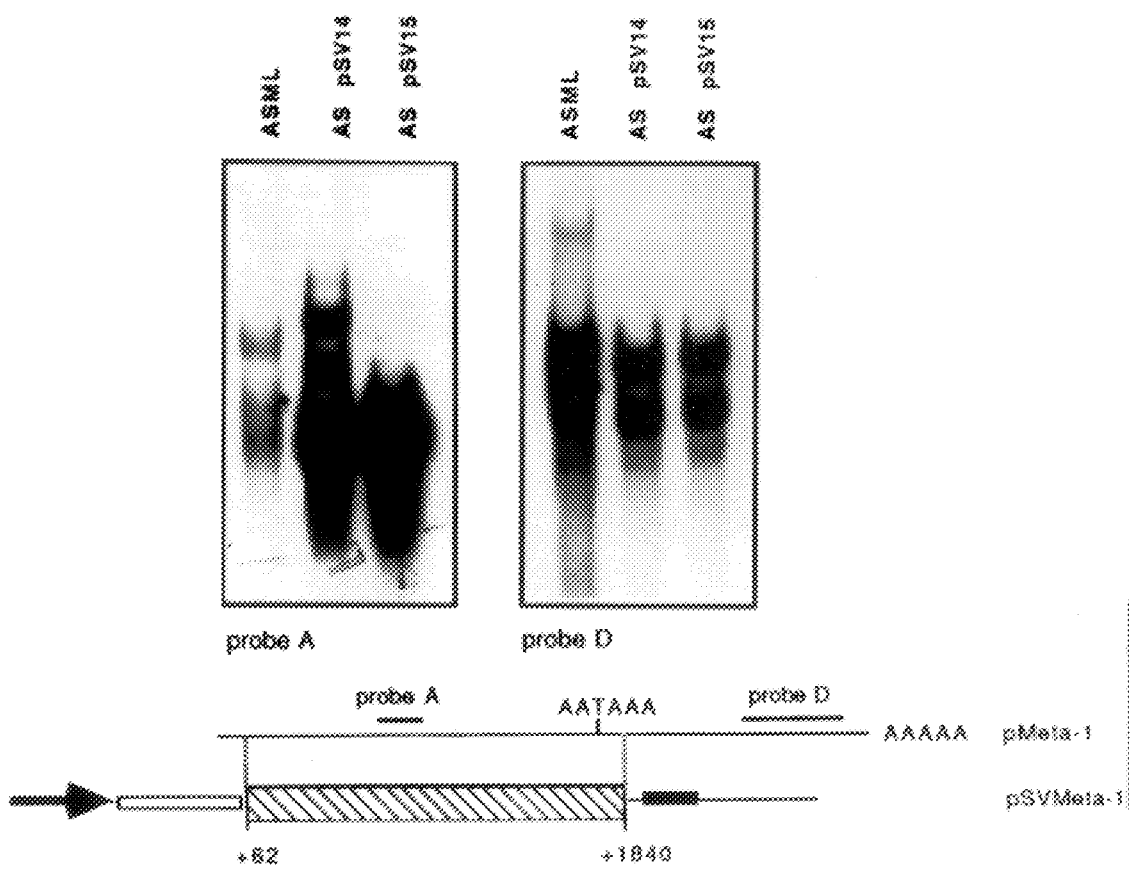

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 3207 base pairs
        ( B ) TYPE: nucleic acid
        ( C ) STRANDEDNESS: double
        ( D ) TOPOLOGY: linear ( v i i ) IMMEDIATE SOURCE:
        ( B ) CLONE: p-Meta-1

( i x ) FEATURE:
        ( A ) NAME/KEY: CDS
        ( B ) LOCATION: 113..1624

( x i ) SEQUENCE DESCRIPTION: SEQ ID NO:1:

```
CTCATTGCCC  AGCAGCCCCC  AGCCAGTGAC  AGGTTCCATT  CACCCTCTTT  GCCCCTTCCC          60

CCGCGACCCT  TTTCCAGAGG  CTACTAGATC  CTTTGGTTTC  ATCCTGCACA  TC ATG            115
                                                              Met
                                                               1

GAC  AAG  GTT  TGG  TGG  CAC  ACA  GCT  TGG  GGA  CTA  CTT  TGC  CTC  TTA  CAG      163
Asp  Lys  Val  Trp  Trp  His  Thr  Ala  Trp  Gly  Leu  Leu  Cys  Leu  Leu  Gln
               5                        10                      15

TTG  AGC  CTG  GCA  CAG  CAG  CAG  ATC  GAT  TTG  AAT  ATA  ACC  TGC  CGT  TAC      211
Leu  Ser  Leu  Ala  Gln  Gln  Gln  Ile  Asp  Leu  Asn  Ile  Thr  Cys  Arg  Tyr
                20                       25                     30

GCA  GGT  GTA  TTC  CAT  GTG  GAG  AAA  AAT  GGC  CGC  TAC  AGT  ATC  TCC  AGG      259
Ala  Gly  Val  Phe  His  Val  Glu  Lys  Asn  Gly  Arg  Tyr  Ser  Ile  Ser  Arg
                35                       40                     45

ACT  GAA  GCA  GCT  GAC  CTC  TGC  GAG  GCT  TTC  AAC  ACC  ACC  TTG  CCC  ACC      307
Thr  Glu  Ala  Ala  Asp  Leu  Cys  Glu  Ala  Phe  Asn  Thr  Thr  Leu  Pro  Thr
50                       55                       60                     65
```

| | | | | | | | | | | | | | | | | |
|---|---|---|---|---|---|---|---|---|---|---|---|---|---|---|---|---|
| ATG | GCT | CAG | ATG | GAG | TTA | GCC | CTG | AGA | AAG | GGG | TTT | GAA | ACA | TGC | AGG | 355 |
| Met | Ala | Gln | Met | Glu | Leu | Ala | Leu | Arg | Lys | Gly | Phe | Glu | Thr | Cys | Arg | |
| | | | 70 | | | | | 75 | | | | | 80 | | | |
| TAT | GGG | TTC | ATA | GAA | GGA | CAC | GTG | GTA | ATC | CCG | AGG | ATC | CAC | CCC | AAC | 403 |
| Tyr | Gly | Phe | Ile | Glu | Gly | His | Val | Val | Ile | Pro | Arg | Ile | His | Pro | Asn | |
| | | | 85 | | | | | 90 | | | | | 95 | | | |
| GCT | ATC | TGT | GCA | GCC | AAC | AAC | ACA | GGA | GTG | TAT | ATC | CTC | CTC | GCA | TCC | 451 |
| Ala | Ile | Cys | Ala | Ala | Asn | Asn | Thr | Gly | Val | Tyr | Ile | Leu | Leu | Ala | Ser | |
| | | 100 | | | | | 105 | | | | | 110 | | | | |
| AAC | ACC | TCC | CAC | TAT | GAC | ACA | TAT | TGC | TTC | AAT | GCC | TCA | GCT | CCT | CTT | 499 |
| Asn | Thr | Ser | His | Tyr | Asp | Thr | Tyr | Cys | Phe | Asn | Ala | Ser | Ala | Pro | Leu | |
| | 115 | | | | | 120 | | | | | 125 | | | | | |
| GAA | GAA | GAC | TGT | ACA | TCA | GTC | ACA | GAC | CTA | CCC | AAT | TCC | TTC | GAT | GGA | 547 |
| Glu | Glu | Asp | Cys | Thr | Ser | Val | Thr | Asp | Leu | Pro | Asn | Ser | Phe | Asp | Gly | |
| 130 | | | | | 135 | | | | | 140 | | | | | 145 | |
| CCA | GTT | ACC | ATA | ACT | ATT | GTC | AAC | CGT | GAT | GGC | ACC | CGC | TAC | AGC | AAG | 595 |
| Pro | Val | Thr | Ile | Thr | Ile | Val | Asn | Arg | Asp | Gly | Thr | Arg | Tyr | Ser | Lys | |
| | | | | 150 | | | | | 155 | | | | | 160 | | |
| AAG | GGC | GAG | TAT | AGA | ACA | CAC | CAA | GAA | GAC | ATC | GAT | GCC | TCA | AAC | ATT | 643 |
| Lys | Gly | Glu | Tyr | Arg | Thr | His | Gln | Glu | Asp | Ile | Asp | Ala | Ser | Asn | Ile | |
| | | | 165 | | | | | 170 | | | | | 175 | | | |
| ATA | GAT | GAG | GAT | GTC | AGC | AGT | GGA | TCC | ACC | ATT | GAG | AAG | AGC | ACC | CCA | 691 |
| Ile | Asp | Glu | Asp | Val | Ser | Ser | Gly | Ser | Thr | Ile | Glu | Lys | Ser | Thr | Pro | |
| | 180 | | | | | 185 | | | | | 190 | | | | | |
| GAA | GGC | TAC | ATT | TTG | CAC | ACC | GAC | CTT | CCC | ACT | TCA | CAG | CCT | ACT | GGA | 739 |
| Glu | Gly | Tyr | Ile | Leu | His | Thr | Asp | Leu | Pro | Thr | Ser | Gln | Pro | Thr | Gly | |
| | 195 | | | | | 200 | | | | | 205 | | | | | |
| GAC | CGG | GAT | GAC | GCC | TTC | TTT | ATT | GGG | AGC | ACC | CTG | GCC | ACC | ATT | GCA | 787 |
| Asp | Arg | Asp | Asp | Ala | Phe | Phe | Ile | Gly | Ser | Thr | Leu | Ala | Thr | Ile | Ala | |
| 210 | | | | | 215 | | | | | 220 | | | | | 225 | |
| ACT | ACT | CCA | TGG | GTT | TCT | GCC | CAC | ACA | AAA | CAG | AAC | CAG | GAA | CGG | ACC | 835 |
| Thr | Thr | Pro | Trp | Val | Ser | Ala | His | Thr | Lys | Gln | Asn | Gln | Glu | Arg | Thr | |
| | | | | 230 | | | | | 235 | | | | | 240 | | |
| CAG | TGG | AAC | CCG | ATC | CAT | TCA | AAC | CCA | GAA | GTA | CTA | CTT | CAG | ACA | ACC | 883 |
| Gln | Trp | Asn | Pro | Ile | His | Ser | Asn | Pro | Glu | Val | Leu | Leu | Gln | Thr | Thr | |
| | | | 245 | | | | | 250 | | | | | 255 | | | |
| ACC | AGG | ATG | ACT | GAT | ATA | GAC | AGA | AAC | AGC | ACC | AGT | GCT | CAT | GGA | GAA | 931 |
| Thr | Arg | Met | Thr | Asp | Ile | Asp | Arg | Asn | Ser | Thr | Ser | Ala | His | Gly | Glu | |
| | | 260 | | | | | 265 | | | | | 270 | | | | |
| AAC | TGG | ACC | CAG | GAA | CCA | CAG | CCT | CCT | TTC | AAT | AAC | CAT | GAG | TAT | CAG | 979 |
| Asn | Trp | Thr | Gln | Glu | Pro | Gln | Pro | Pro | Phe | Asn | Asn | His | Glu | Tyr | Gln | |
| | 275 | | | | | 280 | | | | | 285 | | | | | |
| GAT | GAA | GAG | GAG | ACC | CCA | CAT | GCT | ACA | AGC | ACA | ACC | TGG | GCA | GAT | CCT | 1027 |
| Asp | Glu | Glu | Glu | Thr | Pro | His | Ala | Thr | Ser | Thr | Thr | Trp | Ala | Asp | Pro | |
| 290 | | | | | 295 | | | | | 300 | | | | | 305 | |
| AAT | AGC | ACA | ACA | GAA | GAA | GCA | GCT | ACC | CAG | AAG | GAG | AAG | TGG | TTT | GAG | 1075 |
| Asn | Ser | Thr | Thr | Glu | Glu | Ala | Ala | Thr | Gln | Lys | Glu | Lys | Trp | Phe | Glu | |
| | | | | 310 | | | | | 315 | | | | | 320 | | |
| AAT | GAA | TGG | CAG | GGG | AAG | AAC | CCA | CCC | ACC | CCA | AGT | GAA | GAC | TCC | CAT | 1123 |
| Asn | Glu | Trp | Gln | Gly | Lys | Asn | Pro | Pro | Thr | Pro | Ser | Glu | Asp | Ser | His | |
| | | | 325 | | | | | 330 | | | | | 335 | | | |
| GTG | ACA | GAA | GGG | ACA | ACT | GCC | TCA | GCC | CAC | AAC | AAC | CAT | CCA | AGT | CAA | 1171 |
| Val | Thr | Glu | Gly | Thr | Thr | Ala | Ser | Ala | His | Asn | Asn | His | Pro | Ser | Gln | |
| | | 340 | | | | | 345 | | | | | 350 | | | | |
| AGA | ATG | ACA | ACA | CAG | AGT | CAA | GAG | GAT | GTT | TCA | TGG | ACC | GAT | TTC | TTC | 1219 |
| Arg | Met | Thr | Thr | Gln | Ser | Gln | Glu | Asp | Val | Ser | Trp | Thr | Asp | Phe | Phe | |
| | | 355 | | | | | 360 | | | | | 365 | | | | |
| GAC | CCA | ATC | TCA | CAT | CCA | ATG | GGA | CAA | GGT | CAT | CAA | ACA | GAA | AGC | AAG | 1267 |
| Asp | Pro | Ile | Ser | His | Pro | Met | Gly | Gln | Gly | His | Gln | Thr | Glu | Ser | Lys | |
| 370 | | | | | 375 | | | | | 380 | | | | | 385 | |

| | | | | | | | | | | | | | | | | |
|---|---|---|---|---|---|---|---|---|---|---|---|---|---|---|---|---|
| GGA | CAC | TCA | AGT | GGG | AAT | CAA | GAC | AGT | GGA | GTG | ACC | ACA | ACT | TCT | GGT | 1315 |
| Gly | His | Ser | Ser | Gly | Asn | Gln | Asp | Ser | Gly | Val | Thr | Thr | Thr | Ser | Gly | |
| | | | 390 | | | | | 395 | | | | | | 400 | | |
| CCT | GCG | AGG | AGA | CCT | CAG | ATT | CCA | GAG | TGG | CTT | ATC | ATC | TTG | GCA | TCC | 1363 |
| Pro | Ala | Arg | Arg | Pro | Gln | Ile | Pro | Glu | Trp | Leu | Ile | Ile | Leu | Ala | Ser | |
| | | | 405 | | | | | 410 | | | | | 415 | | | |
| CTC | CTG | GCG | CTG | GCT | CTG | ATT | CTT | GCC | GTC | TGC | ATT | GCT | GTC | AAC | AGT | 1411 |
| Leu | Leu | Ala | Leu | Ala | Leu | Ile | Leu | Ala | Val | Cys | Ile | Ala | Val | Asn | Ser | |
| | | 420 | | | | | 425 | | | | | 430 | | | | |
| AGG | AGA | AGG | TGT | GGG | CAG | AAG | AAG | AAG | CTG | GTG | ATC | AAC | AGT | GGC | AAT | 1459 |
| Arg | Arg | Arg | Cys | Gly | Gln | Lys | Lys | Lys | Leu | Val | Ile | Asn | Ser | Gly | Asn | |
| | | 435 | | | | 440 | | | | | 445 | | | | | |
| GGA | ACA | GTG | GAA | GAC | AGG | AAA | CCA | AGT | GAA | CTC | AAC | GGG | GAG | GCC | AGC | 1507 |
| Gly | Thr | Val | Glu | Asp | Arg | Lys | Pro | Ser | Glu | Leu | Asn | Gly | Glu | Ala | Ser | |
| 450 | | | | | 455 | | | | | 460 | | | | | 465 | |
| AAG | TCT | CAG | GAA | ATG | GTG | CAT | TTG | GTG | AAC | AAG | GAA | CCA | ACA | GAG | ACT | 1555 |
| Lys | Ser | Gln | Glu | Met | Val | His | Leu | Val | Asn | Lys | Glu | Pro | Thr | Glu | Thr | |
| | | | | 470 | | | | | 475 | | | | | 480 | | |
| CCG | GAC | CAG | TTT | ATG | ACA | GCT | GAT | GAG | ACC | CGG | AAT | CTG | CAG | AGT | GTG | 1603 |
| Pro | Asp | Gln | Phe | Met | Thr | Ala | Asp | Glu | Thr | Arg | Asn | Leu | Gln | Ser | Val | |
| | | | 485 | | | | | 490 | | | | | 495 | | | |
| GAT | ATG | AAG | ATT | GGG | GTG | TAGTGCCTAT | GCCACTAACT | TGAAAAGACA | | | | | | | | 1651 |
| Asp | Met | Lys | Ile | Gly | Val | | | | | | | | | | | |
| | | 500 | | | | | | | | | | | | | | |

| | | | | | |
|---|---|---|---|---|---|
| CAACAATTGG | AGACATGTCA | TTACTGGGAG | CTGGGACCCT | TAACAGATGC | AATGTGCTAC | 1711 |
| TGATTATTTT | TTATTGGGAT | TATTTTGGGC | ATAAAATTTC | CCTTTTTTG | TTTTTAAAA | 1771 |
| GTTTGTTTTC | CAATTTATGA | AAATAGCATT | GCTTCTGAA | ATGAGGGTCT | CTTCCAGTTC | 1831 |
| CTCCTTAGAG | GCCTTGCATT | ACCAGGGTAT | GCTACCATAG | GCTTCTACCA | AATGAATACT | 1891 |
| CTTGGTCCCG | ATTGAACCCA | AAGTCCCAGG | TAACATCCAC | CAGCTAAGGA | TTTCCCCAGA | 1951 |
| ACTTAGAGAG | ATTGGTCTCT | GGGAGGAAAT | TTGAATGGGT | CCATATTGCC | TCCCAGCAGT | 2011 |
| CCAATCTGTA | GGCATTGCTT | TGCAGTGGAT | GGGAGATCAG | GTGTACTGGT | TACACACTCT | 2071 |
| CTTTATAGAC | TCCCTTCTGC | TGGAAAATTT | CCACATGCTT | CTGAGAGATT | CCCCAAAGGT | 2131 |
| GACGCTATTT | ATCTTTAGTA | AGCTATTTAT | CTTTGTTTTT | GAAATATCAA | ACCCTGGAGG | 2191 |
| TCCTTTTTTC | AGTATGACTT | TTTTTATTTT | GTTTTTTTT | ATTTGTTTT | TTAGGTTACT | 2251 |
| TTGTCAGAAG | CATAACAGGG | TATAAGTTGA | TTCATAATAA | ATACCTGTCC | ATCTTCCATC | 2311 |
| TTGACCTGTT | GTGCTGTGAT | CCTTCAGTTT | CTAAATCAGC | AAGGTCTGAG | TCTTTGTAGC | 2371 |
| ACATCAATGT | GACCTTAGTA | TGGTCCTCTG | AAACTCATGT | TAGAGCATCC | GTGCCCTGCT | 2431 |
| TGGGTTTACC | CAGCTGAATC | TCAGAAGATC | AAGGACAGGA | GCACTGTTTT | CATTCTAGGA | 2491 |
| CTATCAAAGG | GGTTTCTCTC | CTGTTCAAGA | ATCTGAATTG | GGAGTAGGAG | AGCTTCTGTC | 2551 |
| CCTTTTATGT | TTCGATAACC | ACCCATTTCT | CTTTCTTAAA | GGGCACATTA | AGTTTTTATA | 2611 |
| TCTTACAACA | TTCGCGGTCC | TGTTTCATAG | ACACTGATCT | TATTGGCACT | TTCACAAAAC | 2671 |
| AGTGTGGAGG | GGACTTCTGA | CACCTTATAG | TAAAAGGAGA | AGCCAACAGA | AATGAAAGTG | 2731 |
| TGGACAGAGA | GCAGTAGATT | GGCATGAGGA | GGCATGATGT | ACAACCCCCA | GACCACTCTT | 2791 |
| TCCATCACCA | CATTTGTTGA | TGCTTTCGCA | AGCCAGTTGG | TACTTAGAAT | CAGTTCCCCA | 2851 |
| GGGAATCCTT | CAAAAAGCCA | TAAGAATGCC | CACCCCTGGA | ATCTTACCAC | CACCAGATGA | 2911 |
| GCAGGTTTAT | GGTTTAGCAA | AAGGAGAATG | CTGTCACCCT | CTGACCTCAT | AGTTTTCACA | 2971 |
| TACTGGGCAA | GTGTTCATCT | GCCAGGATGC | CCCATTGCTC | CTAGGTCTTC | CCAGGTACCT | 3031 |
| TGTAGAAGAA | CTTAAATCTA | TAAAATAAGG | CTTTCTCTAA | AATGGAACTT | CCTTTCTAAG | 3091 |

```
GCTCCCATTT TTACTGTTGA CTAAATTTAT ATGTTTAATA GTTTTTTTTC AAATAAAAAC    3151

AAACACAAAA AGGAAAAAAA AAAAAAAAAA AAAAAAAAAA AAAAAAAAAA AAAAA         3207
```

( 2 ) INFORMATION FOR SEQ ID NO:2:

( i ) SEQUENCE CHARACTERISTICS:
        ( A ) LENGTH: 503 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Asp Lys Val Trp Trp His Thr Ala Trp Gly Leu Leu Cys Leu Leu
 1               5                  10                  15

Gln Leu Ser Leu Ala Gln Gln Gln Ile Asp Leu Asn Ile Thr Cys Arg
            20                  25                  30

Tyr Ala Gly Val Phe His Val Glu Lys Asn Gly Arg Tyr Ser Ile Ser
                35                  40                  45

Arg Thr Glu Ala Ala Asp Leu Cys Glu Ala Phe Asn Thr Thr Leu Pro
        50                  55                  60

Thr Met Ala Gln Met Glu Leu Ala Leu Arg Lys Gly Phe Glu Thr Cys
65                  70                  75                  80

Arg Tyr Gly Phe Ile Glu Gly His Val Val Ile Pro Arg Ile His Pro
                85                  90                  95

Asn Ala Ile Cys Ala Ala Asn Asn Thr Gly Val Tyr Ile Leu Leu Ala
                100                 105                 110

Ser Asn Thr Ser His Tyr Asp Thr Tyr Cys Phe Asn Ala Ser Ala Pro
            115                 120                 125

Leu Glu Glu Asp Cys Thr Ser Val Thr Asp Leu Pro Asn Ser Phe Asp
        130                 135                 140

Gly Pro Val Thr Ile Thr Ile Val Asn Arg Asp Gly Thr Arg Tyr Ser
145                 150                 155                 160

Lys Lys Gly Glu Tyr Arg Thr His Gln Glu Asp Ile Asp Ala Ser Asn
                165                 170                 175

Ile Ile Asp Glu Asp Val Ser Ser Gly Ser Thr Ile Glu Lys Ser Thr
            180                 185                 190

Pro Glu Gly Tyr Ile Leu His Thr Asp Leu Pro Thr Ser Gln Pro Thr
            195                 200                 205

Gly Asp Arg Asp Asp Ala Phe Phe Ile Gly Ser Thr Leu Ala Thr Ile
        210                 215                 220

Ala Thr Thr Pro Trp Val Ser Ala His Thr Lys Gln Asn Gln Glu Arg
225                 230                 235                 240

Thr Gln Trp Asn Pro Ile His Ser Asn Pro Glu Val Leu Leu Gln Thr
                245                 250                 255

Thr Thr Arg Met Thr Asp Ile Asp Arg Asn Ser Thr Ser Ala His Gly
            260                 265                 270

Glu Asn Trp Thr Gln Glu Pro Gln Pro Pro Phe Asn Asn His Glu Tyr
        275                 280                 285

Gln Asp Glu Glu Glu Thr Pro His Ala Thr Ser Thr Thr Trp Ala Asp
        290                 295                 300

Pro Asn Ser Thr Thr Glu Glu Ala Ala Thr Gln Lys Glu Lys Trp Phe
305                 310                 315                 320

Glu Asn Glu Trp Gln Gly Lys Asn Pro Pro Thr Pro Ser Glu Asp Ser
                325                 330                 335

His Val Thr Glu Gly Thr Thr Ala Ser Ala His Asn Asn His Pro Ser
```

|  |  |  |  |  | 340 |  |  |  | 345 |  |  |  | 350 |  |  |
|---|---|---|---|---|---|---|---|---|---|---|---|---|---|---|---|
| Gln | Arg | Met<br>355 | Thr | Thr | Gln | Ser | Gln<br>360 | Glu | Asp | Val | Ser | Trp<br>365 | Thr | Asp | Phe |
| Phe | Asp<br>370 | Pro | Ile | Ser | His | Pro<br>375 | Met | Gly | Gln | Gly | His<br>380 | Gln | Thr | Glu | Ser |
| Lys<br>385 | Gly | His | Ser | Ser | Gly<br>390 | Asn | Gln | Asp | Ser | Gly<br>395 | Val | Thr | Thr | Thr | Ser<br>400 |
| Gly | Pro | Ala | Arg | Arg<br>405 | Pro | Gln | Ile | Pro | Glu<br>410 | Trp | Leu | Ile | Ile | Leu<br>415 | Ala |
| Ser | Leu | Leu | Ala<br>420 | Leu | Ala | Leu | Ile | Leu<br>425 | Ala | Val | Cys | Ile | Ala<br>430 | Val | Asn |
| Ser | Arg | Arg<br>435 | Arg | Cys | Gly | Gln | Lys<br>440 | Lys | Lys | Leu | Val | Ile<br>445 | Asn | Ser | Gly |
| Asn | Gly<br>450 | Thr | Val | Glu | Asp | Arg<br>455 | Lys | Pro | Ser | Glu | Leu<br>460 | Asn | Gly | Glu | Ala |
| Ser<br>465 | Lys | Ser | Gln | Glu | Met<br>470 | Val | His | Leu | Val | Asn<br>475 | Lys | Glu | Pro | Thr | Glu<br>480 |
| Thr | Pro | Asp | Gln | Phe<br>485 | Met | Thr | Ala | Asp | Glu<br>490 | Thr | Arg | Asn | Leu | Gln<br>495 | Ser |
| Val | Asp | Met | Lys<br>500 | Ile | Gly | Val |  |  |  |  |  |  |  |  |  |

( 2 ) INFORMATION FOR SEQ ID NO:3:

( i ) SEQUENCE CHARACTERISTICS:
        ( A ) LENGTH: 1062 base pairs
        ( B ) TYPE: nucleic acid
        ( C ) STRANDEDNESS: double
        ( D ) TOPOLOGY: linear ( i i ) MOLECULE TYPE: cDNA ( v i i ) IMMEDIATE SOURCE:
        ( B ) CLONE: human cDNA ( i x ) FEATURE:
        ( A ) NAME/KEY: CDS
        ( B ) LOCATION: 1..1062

( x i ) SEQUENCE DESCRIPTION: SEQ ID NO:3:

| GTA | CAC | CCC | ATC | CCA | GAC | GAA | GAC | AGT | CCC | TGG | ATC | ACC | GAC | AGC | ACA | 48 |
|---|---|---|---|---|---|---|---|---|---|---|---|---|---|---|---|---|
| Val<br>1 | His | Pro | Ile | Pro<br>5 | Asp | Glu | Asp | Ser | Pro<br>10 | Trp | Ile | Thr | Asp | Ser<br>15 | Thr |  |
| GAC | AGA | ATC | CCT | GCT | ACC | ACA | GGC | TGG | GAG | CCA | AAT | GAA | GAA | AAT | GAA | 96 |
| Asp | Arg | Ile | Pro<br>20 | Ala | Thr | Thr | Gly | Trp<br>25 | Glu | Pro | Asn | Glu | Glu<br>30 | Asn | Glu |  |
| GAT | GAA | AGA | GAC | AGA | CAC | CTC | AGT | TTT | TCT | GGA | TCA | GGC | ATT | GAT | GAT | 144 |
| Asp | Glu | Arg<br>35 | Asp | Arg | His | Leu | Ser<br>40 | Phe | Ser | Gly | Ser | Gly<br>45 | Ile | Asp | Asp |  |
| GAT | GAA | GAT | TTT | ATC | TCC | AGC | ACC | ATT | TCA | ACC | ACA | CCA | CGG | GCC | TTT | 192 |
| Asp | Glu<br>50 | Asp | Phe | Ile | Ser | Ser<br>55 | Thr | Ile | Ser | Thr | Thr<br>60 | Pro | Arg | Ala | Phe |  |
| GAC | CAC | ACA | AAA | CAG | AAC | CAG | GAC | TGG | ACC | CAG | TGG | AAC | CCA | AGC | CAT | 240 |
| Asp<br>65 | His | Thr | Lys | Gln | Asn<br>70 | Gln | Asp | Trp | Thr | Gln<br>75 | Trp | Asn | Pro | Ser | His<br>80 |  |
| TCA | AAT | CCG | GAA | GTG | CTA | CTT | CAG | ACA | ACC | ACA | AGG | ATG | ACT | GAT | GTA | 288 |
| Ser | Asn | Pro | Glu | Val<br>85 | Leu | Leu | Gln | Thr | Thr<br>90 | Thr | Arg | Met | Thr | Asp<br>95 | Val |  |
| GAC | AGA | AAT | GGC | ACC | ACT | GCT | TAT | GAA | GGA | AAC | TGG | AAC | CCA | GAA | GCA | 336 |
| Asp | Arg | Asn | Gly<br>100 | Thr | Thr | Ala | Tyr | Glu<br>105 | Gly | Asn | Trp | Asn | Pro<br>110 | Glu | Ala |  |

| | | | | | | | | | | | | | | | |
|---|---|---|---|---|---|---|---|---|---|---|---|---|---|---|---|
| CAC | CCT | CCC | CTC | ATT | CAC | CAT | GAG | CAT | CAT | GAG | GAA | GAA | GAG | ACC | CCA | 384 |
| His | Pro | Pro | Leu | Ile | His | His | Glu | His | His | Glu | Glu | Glu | Glu | Thr | Pro | |
| | 115 | | | | 120 | | | | | 125 | | | | | | |
| CAT | TCT | ACA | AGC | ACA | ATC | CAG | GCA | ACT | CCT | AGT | AGT | ACA | ACG | GAA | GAA | 432 |
| His | Ser | Thr | Ser | Thr | Ile | Gln | Ala | Thr | Pro | Ser | Ser | Thr | Thr | Glu | Glu | |
| 130 | | | | | 135 | | | | | | 140 | | | | | |
| ACA | GCT | ACC | CAG | AAG | GAA | CAG | TGG | TTT | GGC | AAC | AGA | TGG | CAT | GAG | GGA | 480 |
| Thr | Ala | Thr | Gln | Lys | Glu | Gln | Trp | Phe | Gly | Asn | Arg | Trp | His | Glu | Gly | |
| 145 | | | | | 150 | | | | | 155 | | | | | 160 | |
| TAT | CGC | CAA | ACA | CCC | AGA | GAA | GAC | TCC | CAT | TCG | ACA | ACA | GGG | ACA | GCT | 528 |
| Tyr | Arg | Gln | Thr | Pro | Arg | Glu | Asp | Ser | His | Ser | Thr | Thr | Gly | Thr | Ala | |
| | | | | 165 | | | | | 170 | | | | 175 | | | |
| GCA | GCC | TCA | GCT | CAT | ACC | AGC | CAT | CCA | ATG | CAA | GGA | AGG | ACA | ACA | CCA | 576 |
| Ala | Ala | Ser | Ala | His | Thr | Ser | His | Pro | Met | Gln | Gly | Arg | Thr | Thr | Pro | |
| | | | 180 | | | | | 185 | | | | | 190 | | | |
| AGC | CCA | GAG | GAC | AGT | TCC | TGG | ACT | GAT | TTC | TTC | AAC | CCA | ATC | TCA | CAC | 624 |
| Ser | Pro | Glu | Asp | Ser | Ser | Trp | Thr | Asp | Phe | Phe | Asn | Pro | Ile | Ser | His | |
| | | 195 | | | | | 200 | | | | | 205 | | | | |
| CCC | ATG | GGA | CGA | GGT | CAT | CAA | GCA | GGA | AGA | AGG | ATG | GAT | ATG | GAC | TCC | 672 |
| Pro | Met | Gly | Arg | Gly | His | Gln | Ala | Gly | Arg | Arg | Met | Asp | Met | Asp | Ser | |
| | 210 | | | | | 215 | | | | | 220 | | | | | |
| AGT | CAT | AGT | ACA | ACG | CTT | CAG | CCT | ACT | GCA | AAT | CCA | AAC | ACA | GGT | TTG | 720 |
| Ser | His | Ser | Thr | Thr | Leu | Gln | Pro | Thr | Ala | Asn | Pro | Asn | Thr | Gly | Leu | |
| 225 | | | | | 230 | | | | | 235 | | | | | 240 | |
| GTG | GAA | GAT | TTG | GAC | AGG | ACA | GGA | CCT | CTT | TCA | ATG | ACA | ACG | CAG | CAG | 768 |
| Val | Glu | Asp | Leu | Asp | Arg | Thr | Gly | Pro | Leu | Ser | Met | Thr | Thr | Gln | Gln | |
| | | | | 245 | | | | | 250 | | | | | 255 | | |
| AGT | AAT | TCT | CAG | AGC | TTC | TCT | ACA | TCA | CAT | GAA | GGC | TTG | GAA | GAA | GAT | 816 |
| Ser | Asn | Ser | Gln | Ser | Phe | Ser | Thr | Ser | His | Glu | Gly | Leu | Glu | Glu | Asp | |
| | | | 260 | | | | | 265 | | | | | 270 | | | |
| AAA | GAC | CAT | CCA | ACA | ACT | TCT | ACT | CTG | ACA | TCA | AGC | AAT | AGG | AAT | GAT | 864 |
| Lys | Asp | His | Pro | Thr | Thr | Ser | Thr | Leu | Thr | Ser | Ser | Asn | Arg | Asn | Asp | |
| | | 275 | | | | | 280 | | | | | 285 | | | | |
| GTC | ACA | GGT | GGA | AGA | AGA | GAC | CCA | AAT | CAT | TCT | GAA | GGC | TCA | ACT | ACT | 912 |
| Val | Thr | Gly | Gly | Arg | Arg | Asp | Pro | Asn | His | Ser | Glu | Gly | Ser | Thr | Thr | |
| | 290 | | | | | 295 | | | | | 300 | | | | | |
| TTA | CTG | GAA | GGT | TAT | ACC | TCT | CAT | TAC | CCA | CAC | ACG | AAG | GAA | AGC | AGG | 960 |
| Leu | Leu | Glu | Gly | Tyr | Thr | Ser | His | Tyr | Pro | His | Thr | Lys | Glu | Ser | Arg | |
| 305 | | | | | 310 | | | | | 315 | | | | | 320 | |
| ACC | TTC | ATC | CCA | GTG | ACC | TCA | GCT | AAG | ACT | GGG | TCC | TTT | GGA | GTT | ACT | 1008 |
| Thr | Phe | Ile | Pro | Val | Thr | Ser | Ala | Lys | Thr | Gly | Ser | Phe | Gly | Val | Thr | |
| | | | | 325 | | | | | 330 | | | | | 335 | | |
| GCA | GTT | ACT | GTT | GGA | GAT | TCC | AAC | TCT | AAT | GTC | AAT | CGT | TCC | TTA | TCA | 1056 |
| Ala | Val | Thr | Val | Gly | Asp | Ser | Asn | Ser | Asn | Val | Asn | Arg | Ser | Leu | Ser | |
| | | | 340 | | | | | 345 | | | | | 350 | | | |
| GGA | GAC | | | | | | | | | | | | | | | 1062 |
| Gly | Asp | | | | | | | | | | | | | | | |

( 2 ) INFORMATION FOR SEQ ID NO:4:

( i ) SEQUENCE CHARACTERISTICS:
        ( A ) LENGTH: 354 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

| | | | | | | | | | | | | | | |
|---|---|---|---|---|---|---|---|---|---|---|---|---|---|---|
| Val | His | Pro | Ile | Pro | Asp | Glu | Asp | Ser | Pro | Trp | Ile | Thr | Asp | Ser | Thr |
| 1 | | | | 5 | | | | | 10 | | | | | 15 | |
| Asp | Arg | Ile | Pro | Ala | Thr | Thr | Gly | Trp | Glu | Pro | Asn | Glu | Glu | Asn | Glu |
| | | | 20 | | | | | 25 | | | | | 30 | | |

```
Asp Glu Arg Asp Arg His Leu Ser Phe Ser Gly Ser Gly Ile Asp Asp
         35                      40                      45

Asp Glu Asp Phe Ile Ser Ser Thr Ile Ser Thr Thr Pro Arg Ala Phe
         50                      55                      60

Asp His Thr Lys Gln Asn Gln Asp Trp Thr Gln Trp Asn Pro Ser His
65                       70                      75                       80

Ser Asn Pro Glu Val Leu Leu Gln Thr Thr Thr Arg Met Thr Asp Val
                 85                       90                      95

Asp Arg Asn Gly Thr Thr Ala Tyr Glu Gly Asn Trp Asn Pro Glu Ala
             100                     105                     110

His Pro Pro Leu Ile His His Glu His His Glu Glu Glu Thr Pro
             115                     120                     125

His Ser Thr Ser Thr Ile Gln Ala Thr Pro Ser Ser Thr Thr Glu Glu
     130                     135                     140

Thr Ala Thr Gln Lys Glu Gln Trp Phe Gly Asn Arg Trp His Glu Gly
145                      150                     155                     160

Tyr Arg Gln Thr Pro Arg Glu Asp Ser His Ser Thr Thr Gly Thr Ala
             165                     170                     175

Ala Ala Ser Ala His Thr Ser His Pro Met Gln Gly Arg Thr Thr Pro
             180                     185                     190

Ser Pro Glu Asp Ser Ser Trp Thr Asp Phe Phe Asn Pro Ile Ser His
             195                     200                     205

Pro Met Gly Arg Gly His Gln Ala Gly Arg Arg Met Asp Met Asp Ser
         210                     215                     220

Ser His Ser Thr Thr Leu Gln Pro Thr Ala Asn Pro Asn Thr Gly Leu
225                      230                     235                     240

Val Glu Asp Leu Asp Arg Thr Gly Pro Leu Ser Met Thr Thr Gln Gln
             245                     250                     255

Ser Asn Ser Gln Ser Phe Ser Thr Ser His Glu Gly Leu Glu Glu Asp
             260                     265                     270

Lys Asp His Pro Thr Thr Ser Thr Leu Thr Ser Ser Asn Arg Asn Asp
         275                     280                     285

Val Thr Gly Gly Arg Arg Asp Pro Asn His Ser Glu Gly Ser Thr Thr
     290                     295                     300

Leu Leu Glu Gly Tyr Thr Ser His Tyr Pro His Thr Lys Glu Ser Arg
305                      310                     315                     320

Thr Phe Ile Pro Val Thr Ser Ala Lys Thr Gly Ser Phe Gly Val Thr
             325                     330                     335

Ala Val Thr Val Gly Asp Ser Asn Ser Asn Val Asn Arg Ser Leu Ser
             340                     345                     350

Gly Asp
```

( 2 ) INFORMATION FOR SEQ ID NO:5:

( i ) SEQUENCE CHARACTERISTICS:
        ( A ) LENGTH: 355 amino acids
        ( B ) TYPE: amino acid
        ( D ) TOPOLOGY: linear ( v i i ) IMMEDIATE SOURCE:
        ( B ) CLONE: rat protein ( x i ) SEQUENCE DESCRIPTION: SEQ ID NO:5:

```
Ser Gln Pro Thr Gly Asp Arg Asp Asp Ala Phe Phe Ile Gly Ser Thr
1                5                       10                      15

Leu Ala Thr Ser Thr Glu Ser Asn Thr Asn Pro Thr Gly Trp Lys Pro
```

|     |     |     | 20  |     |     |     | 25  |     |     |     | 30  |     |     |     |
| --- | --- | --- | --- | --- | --- | --- | --- | --- | --- | --- | --- | --- | --- | --- |
| Asn | Glu | Glu<br>35 | Asn | Glu | Asp | Glu | Thr<br>40 | Asp | Lys | Tyr | Pro | Asn<br>45 | Phe | Ser | Gly |
| Ser | Gly<br>50 | Ile | Asp | Asp | Asp | Glu<br>55 | Asp | Phe | Ile | Ser | Ser<br>60 | Thr | Ile | Ala | Thr |
| Thr<br>65 | Pro | Trp | Val | Ser | Ala<br>70 | His | Thr | Lys | Gln | Asn<br>75 | Gln | Glu | Arg | Thr | Gln<br>80 |
| Trp | Asn | Pro | Ile | His<br>85 | Ser | Asn | Pro | Glu | Val<br>90 | Leu | Leu | Gln | Thr | Thr<br>95 | Thr |
| Arg | Met | Thr | Asp<br>100 | Ile | Asp | Arg | Asn | Ser<br>105 | Thr | Ser | Ala | His | Gly<br>110 | Glu | Asn |
| Trp | Thr | Gln<br>115 | Glu | Pro | Gln | Pro<br>120 | Phe | Asn | Asn | His | Glu<br>125 | Tyr | Gln | Asp |
| Glu | Glu | Glu<br>130 | Thr | Pro | His | Ala<br>135 | Thr | Ser | Thr | Thr | Trp<br>140 | Ala | Asp | Pro | Asn |
| Ser<br>145 | Thr | Thr | Glu | Glu | Ala<br>150 | Ala | Thr | Gln | Lys | Glu<br>155 | Lys | Trp | Phe | Glu | Asn<br>160 |
| Glu | Trp | Gln | Gly | Lys<br>165 | Asn | Pro | Pro | Thr | Pro<br>170 | Ser | Glu | Asp | Ser | His<br>175 | Val |
| Thr | Glu | Gly | Thr<br>180 | Thr | Ala | Ser | Ala | His<br>185 | Asn | Asn | His | Pro | Ser<br>190 | Gln | Arg |
| Met | Thr | Thr<br>195 | Gln | Ser | Gln | Glu | Asp<br>200 | Val | Ser | Trp | Thr | Asp<br>205 | Phe | Phe | Asp |
| Pro | Ile | Ser<br>210 | His | Pro | Met | Gly<br>215 | Gln | Gly | His | Gln | Thr<br>220 | Glu | Ser | Lys | Asp |
| Thr<br>225 | Gly | Ser | Ser | His | Ser<br>230 | Thr | Thr | Leu | Gln | Pro<br>235 | Thr | Ala | Ala | Pro | Asn<br>240 |
| Thr | His | Leu | Val | Glu<br>245 | Asp | Leu | Asn | Arg | Thr<br>250 | Gly | Pro | Leu | Ser | Val<br>255 | Thr |
| Thr | Pro | Gln | Ser<br>260 | His | Ser | Gln | Asn | Phe<br>265 | Ser | Thr | Leu | Pro | Gly<br>270 | Glu | Leu |
| Glu | Glu | Gly<br>275 | Glu | Asp | His | Pro | Thr<br>280 | Thr | Ser | Val | Leu | Pro<br>285 | Ser | Ser | Thr |
| Lys | Ser<br>290 | Gly | Arg | Arg | Arg | Gly<br>295 | Gly | Ser | Leu | Pro | Arg<br>300 | Asp | Thr | Thr | Thr |
| Ser<br>305 | Leu | Glu | Gly | Tyr | Thr<br>310 | Pro | Gln | Tyr | Pro | Asp<br>315 | Thr | Met | Glu | Asn | Gly<br>320 |
| Thr | Leu | Phe | Pro | Val<br>325 | Thr | Pro | Ala | Lys | Thr<br>330 | Glu | Val | Phe | Gly | Glu<br>335 | Thr |
| Glu | Gly | Thr | Val<br>340 | Ala | Thr | Asp | Ser | Asn<br>345 | Phe | Asn | Val | Asp | Gly<br>350 | Ser | Leu |
| Pro | Gly | Asp<br>355 |

( 2 ) INFORMATION FOR SEQ ID NO:6:

( i ) SEQUENCE CHARACTERISTICS:
    ( A ) LENGTH: 361 amino acids
    ( B ) TYPE: amino acid
    ( D ) TOPOLOGY: linear ( v i i ) IMMEDIATE SOURCE:
    ( B ) CLONE: hCD44

( x i ) SEQUENCE DESCRIPTION: SEQ ID NO:6:

| Met<br>1 | Asp | Lys | Phe | Trp<br>5 | Trp | His | Ala | Ala | Trp<br>10 | Gly | Leu | Cys | Leu | Val<br>15 | Pro |

| | | | | | | | | | | | | | | |
|---|---|---|---|---|---|---|---|---|---|---|---|---|---|---|
| Leu | Ser | Leu | Ala<br>20 | Gln | Ile | Asp | Leu | Asn<br>25 | Ile | Thr | Cys | Arg | Phe<br>30 | Ala | Gly |
| Val | Phe | His<br>35 | Val | Glu | Lys | Asn | Gly<br>40 | Arg | Tyr | Ser | Ile | Ser<br>45 | Arg | Thr | Glu |
| Ala | Ala<br>50 | Asp | Leu | Cys | Lys | Ala<br>55 | Phe | Asn | Ser | Thr | Leu<br>60 | Pro | Thr | Met | Ala |
| Gln<br>65 | Met | Glu | Lys | Ala | Leu<br>70 | Ser | Ile | Gly | Phe | Glu<br>75 | Thr | Cys | Arg | Tyr | Gly<br>80 |
| Phe | Ile | Glu | Gly | His<br>85 | Val | Val | Ile | Pro | Arg<br>90 | Ile | His | Pro | Asn | Ser<br>95 | Ile |
| Cys | Ala | Ala | Asn<br>100 | Asn | Thr | Gly | Val | Tyr<br>105 | Ile | Leu | Thr | Tyr | Asn<br>110 | Thr | Ser |
| Gln | Tyr | Asp<br>115 | Thr | Tyr | Cys | Phe | Asn<br>120 | Ala | Ser | Ala | Pro | Pro<br>125 | Glu | Glu | Asp |
| Cys | Thr<br>130 | Ser | Val | Thr | Asp | Leu<br>135 | Pro | Asn | Ala | Phe | Asp<br>140 | Gly | Pro | Ile | Thr |
| Ile<br>145 | Thr | Ile | Val | Asn | Arg<br>150 | Asp | Gly | Thr | Arg | Tyr<br>155 | Val | Gln | Lys | Gly | Glu<br>160 |
| Tyr | Arg | Thr | Asn | Pro<br>165 | Glu | Asp | Ile | Tyr | Pro<br>170 | Ser | Asn | Pro | Thr | Asp<br>175 | Asp |
| Asp | Val | Ser | Ser<br>180 | Gly | Ser | Ser | Ser | Glu<br>185 | Arg | Ser | Ser | Thr | Ser<br>190 | Gly | Gly |
| Tyr | Ile | Phe<br>195 | Tyr | Thr | Phe | Ser | Thr<br>200 | Val | His | Pro | Ile | Pro<br>205 | Asp | Glu | Asp |
| Ser | Pro<br>210 | Trp | Ile | Thr | Asp | Ser<br>215 | Thr | Asp | Arg | Ile | Pro<br>220 | Ala | Thr | Arg | Asp |
| Gln<br>225 | Asp | Thr | Phe | His | Pro<br>230 | Ser | Gly | Gly | Ser | His<br>235 | Thr | Thr | His | Glu | Ser<br>240 |
| Glu | Ser | Asp | Gly | His<br>245 | Ser | His | Gly | Ser | Gln<br>250 | Glu | Gly | Gly | Ala | Asn<br>255 | Thr |
| Thr | Ser | Gly | Pro<br>260 | Ile | Arg | Thr | Pro | Gln<br>265 | Ile | Pro | Glu | Trp | Leu<br>270 | Ile | Ile |
| Leu | Ala | Ser<br>275 | Leu | Leu | Ala | Leu | Ala<br>280 | Leu | Ile | Leu | Ala | Val<br>285 | Cys | Ile | Ala |
| Val | Asn<br>290 | Ser | Arg | Arg | Arg | Cys<br>295 | Gly | Gln | Lys | Lys | Lys<br>300 | Leu | Val | Ile | Asn |
| Ser<br>305 | Gly | Asn | Gly | Ala | Val<br>310 | Glu | Asp | Arg | Lys | Pro<br>315 | Ser | Gly | Leu | Asn | Gly<br>320 |
| Glu | Ala | Ser | Lys | Ser<br>325 | Gln | Glu | Met | Val | His<br>330 | Leu | Val | Asn | Lys | Glu<br>335 | Ser |
| Ser | Glu | Thr | Pro<br>340 | Asp | Gln | Phe | Met | Thr<br>345 | Ala | Asp | Glu | Thr | Arg<br>350 | Asn | Leu |
| Gln | Asn | Val | Asp<br>355 | Met | Lys | Ile | Gly<br>360 | Val | | | | | | | |

( 2 ) INFORMATION FOR SEQ ID NO:7:

( i ) SEQUENCE CHARACTERISTICS:
        ( A ) LENGTH: 363 amino acids
        ( B ) TYPE: amino acid
        ( D ) TOPOLOGY: linear ( v i i ) IMMEDIATE SOURCE:
        ( B ) CLONE: mCD44

( x i ) SEQUENCE DESCRIPTION: SEQ ID NO:7:

| | | | | | | | | | | | | | | |
|---|---|---|---|---|---|---|---|---|---|---|---|---|---|---|
| Met 1 | Asp | Lys | Phe | Trp 5 | Trp | His | Thr | Ala | Trp 10 | Gly | Leu | Cys | Leu | Gln 15 |
| Leu | Ser | Leu | Ala 20 | His | Gln | Gln | Ile 25 | Asp | Leu | Asn | Val | Thr 30 | Cys | Arg | Tyr |
| Ala | Gly | Val 35 | Phe | Cys | Val | Glu | Lys 40 | Asn | Gly | Arg | Tyr | Ser 45 | Ile | Ser | Arg |
| Thr | Glu 50 | Ala | Ala | Asp | Leu | Cys 55 | Gln | Ala | Phe | Asn | Ser 60 | Thr | Leu | Pro | Thr |
| Met 65 | Asp | Gln | Met | Lys | Leu 70 | Ala | Leu | Ser | Lys | Gly 75 | Phe | Glu | Thr | Cys | Arg 80 |
| Tyr | Gly | Phe | Ile | Glu 85 | Gly | Asn | Val | Val | Ile 90 | Pro | Arg | Ile | His | Pro 95 | Asn |
| Ala | Ile | Cys | Ala 100 | Ala | Asn | His | Thr | Gly 105 | Val | Tyr | Ile | Leu | Val 110 | Thr | Ser |
| Asn | Thr | Ser 115 | His | Tyr | Asp | Thr | Tyr 120 | Cys | Phe | Asn | Ala | Ser 125 | Ala | Pro | Pro |
| Glu | Glu 130 | Asp | Cys | Thr | Ser | Val 135 | Thr | Asp | Leu | Pro | Asn 140 | Ser | Phe | Asp | Gly |
| Pro 145 | Val | Thr | Ile | Thr | Ile 150 | Val | Asn | Arg | Asp | Gly 155 | Thr | Arg | Tyr | Ser | Lys 160 |
| Lys | Gly | Glu | Tyr | Arg 165 | Thr | His | Gln | Glu | Asp 170 | Ile | Asp | Ala | Ser | Asn 175 | Ile |
| Ile | Asp | Asp | Asp 180 | Val | Ser | Ser | Gly | Ser 185 | Thr | Ile | Glu | Lys | Ser 190 | Thr | Pro |
| Glu | Gly | Tyr 195 | Ile | Leu | His | Thr | Tyr 200 | Leu | Pro | Thr | Glu | Gln 205 | Pro | Thr | Gly |
| Asp | Gln 210 | Asp | Asp | Ser | Phe | Phe 215 | Ile | Arg | Ser | Thr | Leu 220 | Ala | Thr | Arg | Asp |
| Arg 225 | Asp | Ser | Ser | Lys | Asp 230 | Ser | Arg | Gly | Ser | Ser 235 | Arg | Thr | Val | Thr | His 240 |
| Gly | Ser | Glu | Leu | Ala 245 | Gly | His | Ser | Ser | Ala 250 | Asn | Gln | Asp | Ser | Gly 255 | Val |
| Thr | Thr | Thr | Ser 260 | Gly | Pro | Met | Arg | Arg 265 | Pro | Gln | Ile | Pro | Glu 270 | Trp | Leu |
| Ile | Ile | Leu 275 | Ala | Ser | Leu | Leu | Ala 280 | Leu | Ala | Leu | Ile | Leu 285 | Ala | Val | Cys |
| Ile | Ala 290 | Val | Asn | Ser | Arg | Arg 295 | Arg | Cys | Gly | Gln | Lys 300 | Lys | Lys | Leu | Val |
| Ile | Asn 305 | Gly | Gly | Asn | Gly | Thr 310 | Val | Glu | Asp | Arg | Lys 315 | Pro | Ser | Glu | Leu 320 |
| Asn | Gly | Glu | Ala | Ser 325 | Lys | Ser | Gln | Glu | Met 330 | Val | His | Leu | Val | Asn 335 | Lys |
| Glu | Pro | Ser | Glu | Thr 340 | Pro | Asp | Gln | Cys | Met 345 | Thr | Ala | Asp | Glu 350 | Thr | Arg |
| Asn | Leu | Gln | Ser 355 | Val | Asp | Met | Lys | Ile 360 | Gly | Val | | | | | |

( 2 ) INFORMATION FOR SEQ ID NO:8:

( i ) SEQUENCE CHARACTERISTICS:
        ( A ) LENGTH: 23 amino acids
        ( B ) TYPE: amino acid
        ( D ) TOPOLOGY: linear ( v i i ) IMMEDIATE SOURCE:
        ( B ) CLONE: rCD44

(xi) SEQUENCE DESCRIPTION: SEQ ID NO:8:

```
Ser  Asp  Gly  Asp  Ser  Ser  Met  Asp  Pro  Arg  Gly  Gly  Phe  Asp  Thr  Val
1                   5                        10                       15

Thr  His  Gly  Ser  Glu  Leu  Ala
                    20
```

ANTIBODIES THAT REACT WITH VARIANT CD44 SURFACE PROTEINS

This application is a division, of application Ser. No. 07/946,497, filed Nov. 9, 1992, now U.S. Pat. No. 5,506,119, which is the national state of PCT/EP91/00614 filed Mar. 30, 1991.

The invention concerns variant CD44 surface proteins, antibodies against the variant determinants of these proteins, as well as processes for their production, furthermore the DNA sequences which code for these variant protein fragments, as well as the use of these proteins or parts thereof and the antibodies directed against there for the diagnosis and therapy of tumour metastases.

BACKGROUND OF THE INVENTION

The ability to metastase forms the actual life-endangering property of malignant tumour cells. The original primary tumour cells probably acquire this property by a whole series of changes in the course of the tumour progression. As a result of this process, cancer cell variants are continuously detached from the primary tumour mass, penetrate the extracellular matrix and migrate into the lymphatic system or the blood circulation. Often adhering to one another, the metastasing tumour cells are transported in the blood or lymph system, leave the vascular system at other places in order there to penetrate into secondary tissue and form daughter tumours (survey of Hart et al., 1989; Nicolson, 1987). The formation of metastases requires a whole series of interactions of the tumour cells with intercellular matrix and other cells. Almost all of these interactions require cell surface components, such as e.g. the receptors for matrix and lamina, surface-bound proteolytic enzymes, as well as cell adhesion molecules with inclusion of those which cause organ-specific adhesion and thus organ preference of the metastasis, furthermore growth factors and growth factor receptors.

It is known that the membrane proteins differentiate non-metastasing and metastasing tumour cells of the BSp73 rat tumours, demonstrated by antibody reaction (Matzku et al., 1983 and 1989).

SUMMARY OF THE INVENTION

It has now been found that the metastasizing BSp73ASML tumour cells contain a surface protein which, in part, corresponds to a known glycoprotein participating in the lymphocyte adhesion and cell-cell and cell-matrix exchange action (designation of the normal glyco-protein in humans: CD44, hermes-1, in the mouse: Ppg-1 and in the rat: HEBF1n). However, the new variant CD44 surface protein differs from these known sequences by an extracellular region (ECR) of 154 amino acids which is introduced between the 220th and 237th amino acid of the human CD44 sequence (or 224th and 239th amino acid of the mouse sequence). This new glycoprotein appears is to possess an important role for the cell/matrix or cell/cell binding in the case of the metastasis. Therefore, the production and characterisation of this protein region (ECR) forms one of the tasks of the present invention. By immunisation of mice with membrane proteins which have been obtained from BSp73ASML, spleen cells were produced which form antibodies against the ECR of the variant CD44 surface protein. According to the method of Köhler (1981), these are fused by polyethylene glycol with myeloma cells in order to produce permanent cultures. By means of cloning and selection of those cultures which produce antibodies which react with BSp73ASML but not with the non-metastasing parent form and also not with other non-tumorigenic rat cells, there can be obtained specific antibodies against the new protein part ECR. For the further investigation, a monoclonal antibody was chosen which stains the BSp73ASML cells in the immunofluorescence test especially intensively, which has received the designation mAb1.1ASML (mAb: monoclonal antibody).

In the Western blot test, in a protein hydrolysate from BSp73ASt4L, there can be determined 4 protein bands with molecular weights of 120,000; 150,000; 180,000 and 200,000 with mAb1.1.ASML, whereas extracts from rat fibroblast cells and non-metastasing rat tumour cells give no significant reaction. It has not yet been possible to determine whether these size differences are due to a different original amino acid sequence or to a differently strong subsequent protein modification. In any case, the epitope recognised by the antibody is contained in all 4 protein species but not in the proteins serving for the control from the non-metastasing BSp73As cells or from normal rat cells.

Isolation of cDNA sequences which code for the ECR of the surface protein

The monoclonal antibody mAb1.1ASML is produced by the hybridoma 1.1 ASML deposited as Accession Number DSM ACC 2363 at the Deutsche Sammlung von Mikroorganismen and Zellkulturen GmbH, Mascheroder Weg 1b, D-38124 Braunschweig, Germany. The mAb1.1 ASML was used in order to discover the ECR-coding cDNA sequences in a bacterial expression bank. The bank was constructed with the help of PolyA+ RNA from BSp73ASML and the pEX vector system (Stanley & Luzio, 1984). The products coded by the cDNA sequences are found as β-galactosidase fusion proteins with the help of the antibodies. A so-isolated cDNA clone positive for the monoclonal antibody 1.1ASML with the name pEX34 carries a cDNA sequence piece of 167 nucleotides. This cDNA piece was now used in order to pattern through a larger cDNA bank in the vector pSP65, again from BSp73ASML RNA. One of these clones isolated therewith, pM66, served thereto to isolate the total length cDNA clone pMeta-1 with the help of so-called "primer" elongation (starter oligonucleotides) and of the polymerase chain reaction (PCR). Evidence of the total length was obtained with the help of the primary elongation (3207 nucleotides). The colinearity with an RNA from the BSp73ASML tumour was documented by RNase and S1 protection analysis.

BRIEF DESCRIPTION OF THE FIGURES

FIGS. 2a –2h depict the sequence of the CD44 protein (SEQ ID NO:2) and DNA (SEQ ID NO:1) from p-Meta-1. The signal peptide is represented by ". . . ". The ECR is represented by "–". The transmembrane region is represented by "\\\\\".

FIGS. 3a(1)–3a(4) depict the nucleotide (SEQ ID No. 3) and protein (SEQ ID No. 2) sequence of a human extracellular region and compares the protein sequence to a rat sequence.

FIGS. 3b(1)–3b(3) depict the comparison of protein sequences of rat rMeta-1, human hCD∴ and mouse lllCD44.

FIG. 5 depicts RNA patterns from G418-resistant and p-Meta-1 expressing BSp73AS cells.

DETAILED DESCRIPTION OF PREFERRED EMBODIMENTS

The isolation of the cDNAs with the help of the expression in bacteria and the recognition by the antibodies proved that the antibody recognised primary amino acid sequence in the FCR of the surface protein.

ECR-coding messenger RNA is expressed in BSp73ASML but not in BSp73AS cells

Figure 1:
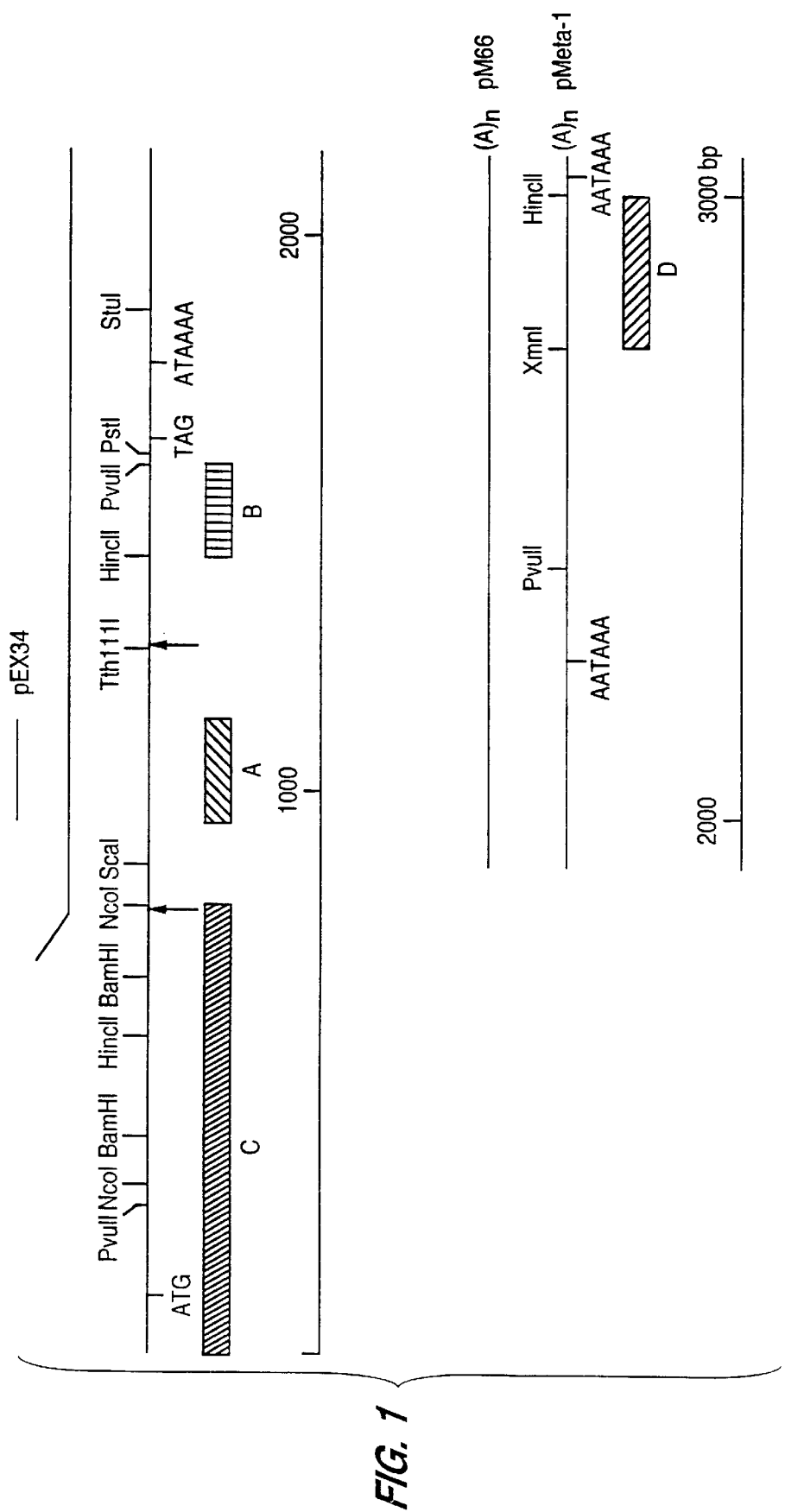
FIG. 1 depicts the structure of a cDNA of the rat surface protein p-Meta-1. Bar "A" represents the extracellular region ("ECR") at positions 941–1108. Bar "B" represents the sequence between positions 1403–1572. Bar "C" represents the sequence between the starting position to position 794. Bar "D" represents sequences at the end of the cDNA clone.
Figure 2D:
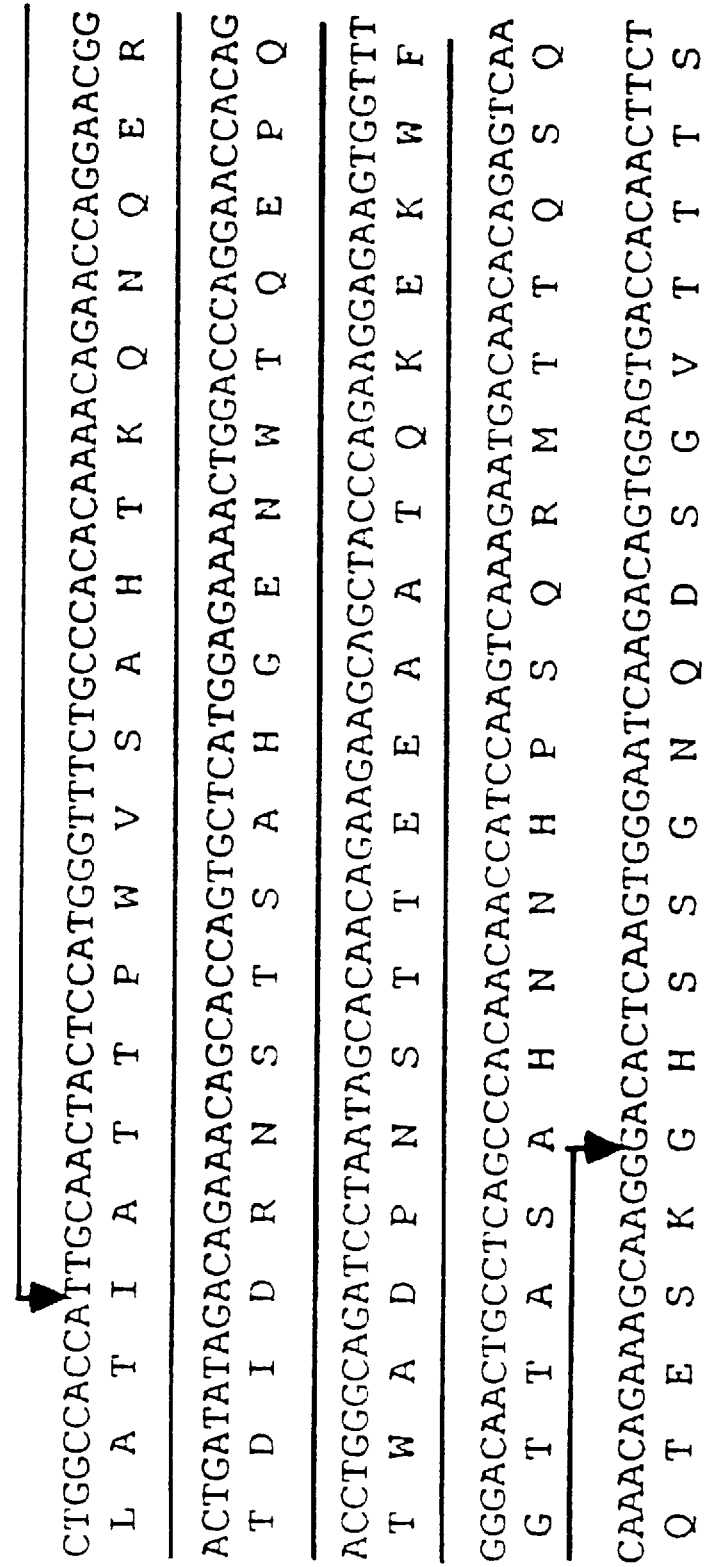

Three different sequence samples were produced from the cDNA clones in order to demonstrate specific messenger RNAs by hybridisation. A sample A covers the cDNA region which codes for the ECR (positions: 941–1108). The sample B represents sequences between the positions 1403–1572 and sample C carries sequences from the start up to position 794 from pMeta-L (FIG. 1). Poly A+ RNA of the BSp73 tumour cell line was separated electrophoretically and analysed with the help of RNA transfer hybridisation. Four of the cell lines, which do not metastase, contain no RNA which is homologous to the sample A, whereas RNAs from the metastasing tumour cells strongly react BSp73ASML. In this RNA preparation, the sample A recognises a heterogenous mixture of various RNA sizes between 2.2 and 3.3 kb and a larger RNA species of 4.9 kb. The exclusive expression of the specific membrane proteins recognised by the monoclonal antibody 1.1ASML in the metastasing tumour cell variant is obviously based upon the exclusive expression of the corresponding ECR-coding messenger RNAs. Obviously the complete cDNA clone pMeta-1 with 3.2 kb cannot represent all sequences of this RNA species. It can only represent one species from the heterogenous mixture of RNA sizes. The samples B and C give the same hybridisation pattern as sample A in the separation of the BSp73ASML RNA in any case as far as one can ascertain in the heterogeneity, i.e. these RNA species carry sequences which are complementary to all three samples, A, B and C. In contradistinction to sample A, sample B and C also recognise messenger RNA species in the non-metastasing cell lines. However, the RNA sizes differ clearly from those in BSp73ASML, there are, namely, detected four clearly differentiatable messenger RNA species with the sizes 1.5, 2.0, 2.9 and 4.3 kb. Although these RNA species could be hidden in the heterogenous mixture of the RNAs from BSp73ASML, it is, nevertheless, certain that they do not exist in the same amount in the BSp73ASML. It is decisive that RNA sequences with complementarity to sample A are obviously completely absent in the non-metastasing cells. Therefore, we can carefully conclude that the sequences of the samples A, B and C are contained in the same RNAs in the metastasing tumour, namely, in a manner as though sample A sequences have been spliced into the B-C-positive RNAs and as though this alternative splicing process only occurred in the metastasing cell line.

In order to demonstrate the colinearity between RNA and cDNA and in order to analyse the difference of the RNAs between the BSp73AS and the BSp73ASML cells, S1 nuclease and RNase protection analyses were carried out. The protected DNA or RNA fragments could only be smaller than the total length because they contain 5'-end vector sequences which cannot hybridise with the RNAs from the tumour cells. We consider first the transfer to the 3' side: the transfer of sequences with homology to sample A to those to sample B. Both techniques show a single RNA species in BSp73AS which is colinear with the samples over a wide range. Furthermore, 5' thereof differentiate cDNA or RNA sample, which certainly correspond to RNA sequences from BSp73ASML, from the RNA from the BSp73AS cells. In particular, the RNAs from BSp73ASML contain sequences which protect larger fragments of the samples. The largest fragments correspond to the full length of the DNA or RNA pieces which were offered for the protection analysis. Smaller fragments are also detectable. Since the RNA transfer hybridisations have certainly uncovered a heterogenous mixture of different sizes of RNAs, it is possible that these indicate smaller protected fragments of RNA species which diverge elsewhere from the cDNA, i.e. at positions between the previously detected divergence point and the 5' end of the offered samples. The RNA species are also not detectable in the BSp73AS cells.

We now consider the point of the divergence on the 5' side, thus the transition of sequences which hybridise with the sample C to those which hybridise with the sample A, thus the ECR-coding sequence. The analysis gives corresponding results for the 5' breaking point. RNAs from BSp73AS can protect the offered samples only over a small range. Messenger RNAs from BSp73ASML protect longer fragments. They are, namely, colinear over the whole length of the offered sample. One can thus conclude that the cDNA clone represents pMeta-1 sequences which are distinctive in the metastasing tumour cells BSp73ASML. The 3' and 5' regions are also found in RNAs from BSp73AS. The ECR-coding sequences with the definite transitions, which can be mapped with the help of these above-described techniques, indicate that here an alternative splicing mechanism must be present for the RNA formation. The 5' and 3' breakage points of the transitions to the ECR sequences are marked by arrows in FIG. 1.

The monoclonal antibody 1.1ASML identifies a variant form of the glycoprotein CD44

In order to obtain structural information about the surface protein, all cloned cDNA molecules have been sequenced. The nucleotide sequence of the total length clone pMeta-1 and the amino acid sequences derived therefrom are shown in FIGS. 2a–2h (SEQ ID NOS 1 and 2). The total length cDNA clone traverses 3207 nucleotides (SEQ ID NO:1). The 3' terminus carries a PolyA end, two additional polyadenylation signals lie at positions 2288 and 1743. The first ATG codon follows a consensus initiation sequence and opens a reading frame of 1509 nucleotides, corresponding to 503 amino acids (SEQ ID NO:1). As one should assume for a membrane-standing protein, the first 21 amino acids are hydrophobic and represent a signal peptide. No part of these sequences is hitherto to be found in the data bases. However, we found sequence homology to the recently published data about the lymphocyte homing receptor CD44 (of Pgp-1) (Idzerda et al., 1989; Goldstein et al., 1989; Stamenkovic et al., 1989; Nottenburg et al., 1989; Zhou et al., 1989). The homologies are strictly limited to the 5' and 3' parts of the cDNA with inclusion of non-translated regions and they end at the already above-mentioned points of divergence between the BSp73AS and the BSp73ASML RNA sequences. The total extent between the divergence points (in FIGS. 2a–2h characterised by colour markings), thus the whole extent of the metastasis-specific ECR-coding sequence, is not represented in the Pgp1 or CD44 sequences. The metastasis-specific glycoprotein obviously represents a variant of the CD44 glycoproteins. It carries, namely, an additional extracellular domain of 156 amino acids and thus an expanded extracellular region of 410 amino acids (less 21 amino acid signal peptide), in comparison with 270 amino acids (also less signal peptide) of the unchanged CD44 glycoprotein. However, in the non-metastasing BSp73AS cells, the unchanged forms of this CD44 family are detected. cDNA sequences of these BSp73AS RNAs have also been cloned and the identity with the metastasis-specific clones outside of the extra domain is demonstrated.

The expression of the variant CD44 is correlated with the metastatic potential.

In order to test whether the expression of the variant CD44 glycoproteins takes place without exception in the BSp73ASML cells and whether it stands in connection with the metastatic potential of these cells or with the metastatic potential in general, we studied a series of isogenic rat tumour cell lines, namely, the tumour cell lines of the mammary carcinoma system 13762 NF (Neri et al., 1982). We here compare cell lines which have been derived from the parental tumour, namely, the MTPa, MTC, MTP7 and MTA cells (group 1), with cell lines which were established front lymph nodes or lung metastases, namely, MTLy, MTLn2, MTLn3 (group 2). The group 1 cells essentially express the normal CD44 pattern similarly to the RNAs from the BSp73AS cells when one hybridises with sample B. On the other hand, with sample A, there is detected a smaller amount of a diffuse RNA band which has about the size 2.5 kb. On the other hand, the group 2 cells show a completely different RNA pattern. Both samples A and B hybridise with larger RNA species. The sizes resemble those which are detected with BSp73ASML. The similarity is also documented by RNAse and S1 protection analyses. On the basis of these data, we conclude that a change of the splicing pattern of the RNA and the expression of variant CD44 is correlated with the formation of metastases and that the acquired pattern in these metastasing mammary carcinoma cells corresponds very much to those which we have already got to know for the metastasing BSp73ASML cell line. The high molecular proteins recognised by the antibodies correspond to the two high molecular species of proteins which were detected in the BSp73ASML extracts. In this mammary tumour series, we thus discovered also a metastasis-specific expression of RNA species and of high molecular proteins. That in the group 1, thus the so-called parenteral cell lines, any RNAs were found at all which hybridised with the sample A, thus the ECR-coding sequence, and that we can also see a weak coloration of a protein of 100,000 Dalton with the antibody, we attribute to the fact that the group 1 cells also possess small metastasing ability quite contrary to our original cell line BSp73AS which shows no metastasing behaviour at all.

The monoclonal antibody 1.1ASML inhibits metastasis formation in the rat

In a series of experiments for the metastasis formation of the tumour cell line BSp73ASML in isogenic rats, cells were injected subcutaneously and at different times the monoclonal antibody 1.1ASML was injected intraperitoneally at intervals of two to three days before and after the tumour administration. In the scope of this immunological protocol, it was also determined how the immune response of the rat towards the injected antibody had taken place. There result, namely, anti-mouse immunoglobulin antibodies, as well as also anti-idiotype antibodies. The result of this series of experiments is that the growth and the metastasing of the tumour is considerably delayed by injection of 1.1ASML. This delay permits, in its kinetic, the conclusion that the antibody interferes with a primary process of the metastasing. The experiment shows to us that the protein structure on the surface of the metastasirg cells recognised by the antibody has a role in the metastasing process and that therapeutic and diagnostic plans are realistic.

Isolation of the homologous human sequence for the ECR-coding sequence part of the rat cDNA For human tumour cells in culture, the possibility naturally does not exist as a matter of course of detecting, correspondingly the rat system, whether they also still retain metastasing properties. Experiments with immune-deficient mice make possible only very limited predictions regarding the metastasis potential in the case of humans. Therefore, relatively many tumour cell lines, which have been taken up in culture anywhere in the world at points of time lying a long time ago, would have to be tested for whether they express the sequences which we could detect for the rat metastases. It has been possible to find such a tumour cell line. It originates from a large-cell lung carcinoma of humans and bears the number: LCLC97. In this tumour cell line can be detected three definite RNA species (sizes: 5.5; 3.4 and 2.8 kb) which behave quite corresponding to the RNAs which are detectable in the metastasing tumour cell lines of the rat. They hybridise, namely, not only with the sample A but also with the samples B and C, i.e. that also these human RNA species are identical over wide ranges to the cDNA pMeta-1 (85%).

Figure 3B-2:
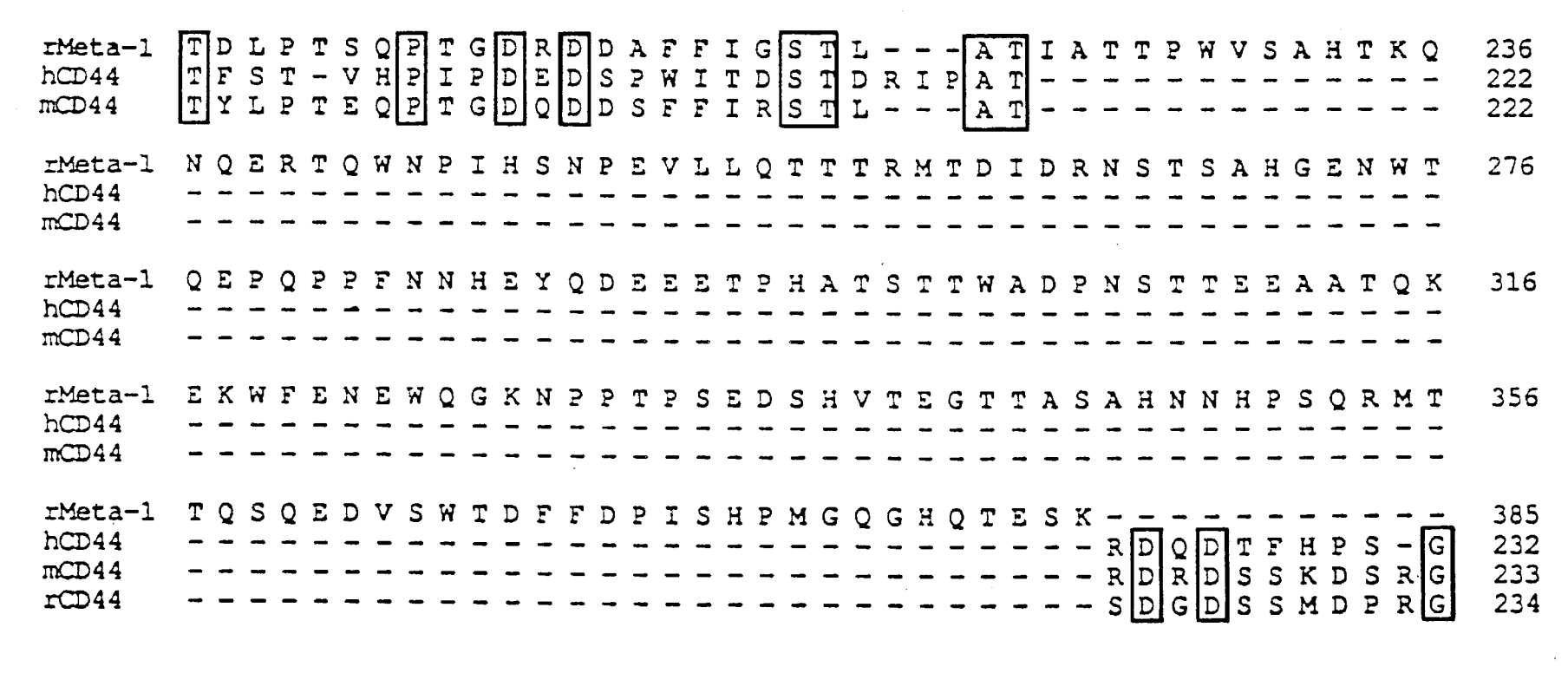
Figure 3B-3:
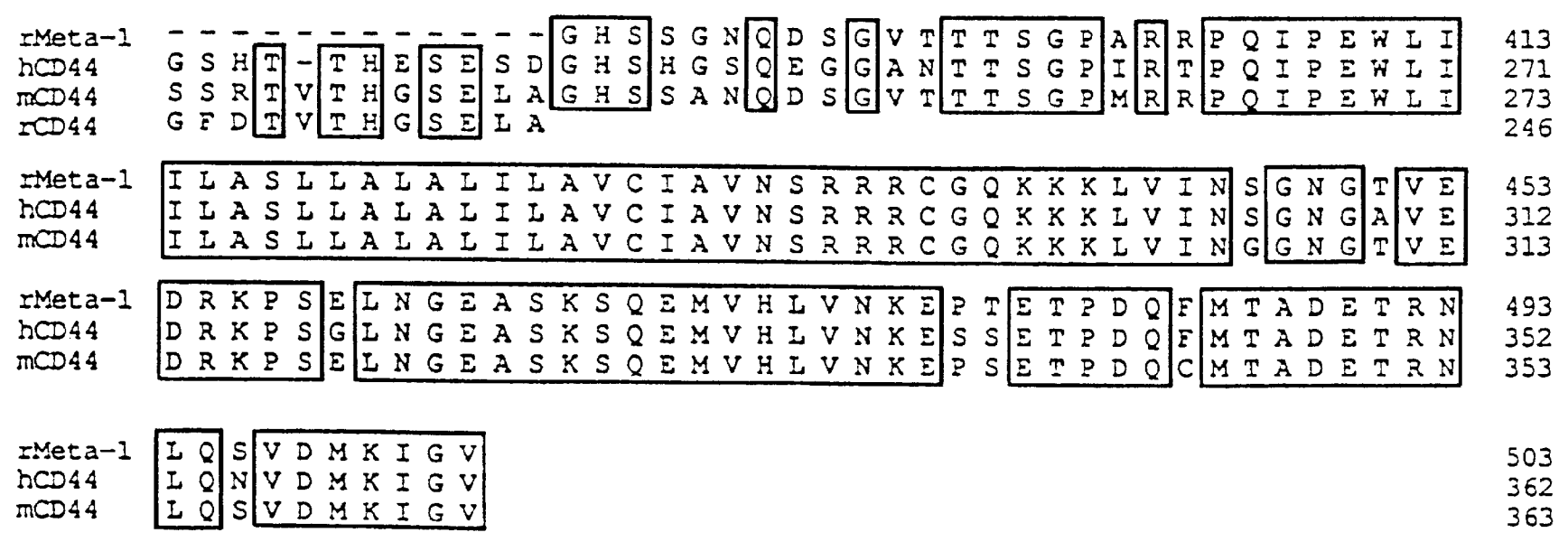

However, the monoclonal antibody 1.1ASML does not react with this tumour cell, i.e. the piece of protein recognised by the antibody must, in the region of the antigen determinant, differ from the proteins which exist on the surface of the human tumour cells. For the non-reactivity, there suffice already the smallest variations on the basis of the high specificity of the antibody. The human tumour cell LCLC97 now served the purpose of constructing a cDNA bank. On the basis of the high agreement between the rat and human sequences, a cDNA clone could be isolated which showed homology with the sample A. The human cDNA was sequenced. In FIGS. 3a(1)–3b(4) and 3b(1)–3b(3) are shown the primary sequence and the amino acid sequence (SEQ ID NOS 3 and 4) derived therefrom. One can see that, over large regions, identity exists between the rat (SEQ ID NO:5) and the human sequence. This human sequence (SEQ ID NO:3), as well as also the amino acid sequence (SEQ ID NO:4) derived therefrom, is also the subject of this Patent Specification. FIGS. 3b(1)–3b(3) also shows the protein sequences of surface proteins for rate (rMeta-1, SEQ ID NO:2) human (hCD44, SEQ ID NO:6) and mouse (mCD44, SEQ ID NO:7) with extracellular regions in rat and human protein. rCD44 (SEQ ID NO:8) is also shown in this Figure.

Embodimental examples

Cells and antibodies

The following cloned Bsp cell lines were used for the investigation: BSp73 14ASML-1 and 10AS-7 and kept in culture as described by Matzku et al., (1983); furthermore, the mammary carcinoma cell lines described by Neri et al., (1982), monoclonal antibodies against BSp73 ASML membrane proteins were produced by immunisation of Balb c nice. After isolation of the spleen cells of an immunised mouse, these were fused with Ag8 myeloma cells for the immortalisation according to the method for the production of monoclonal antibodies of Köhler (1981). The then-obtained hybridoma cells were subjected to a screening process in order to find those which produce specific antibodies against BSp73ASML but not against BSp73AS and normal rat fibroblast cells. The precise procedure is described in the same way as by Matzku et al. (1989).

Monoclonal antibody (mAb)-producing hybridoma cells with the corresponding specificity were expanded in the tissue culture and the mAb given off into the medium highly enriched by ammionium sulphate precipitation and column chromatography (protein A-Sepharose and MonoQ) and used in this form for the investigations. One of them is mAb1.1ASML.

Immunofluorescence

For the display of the variant CD44 molecule on different tumour cells, these were taken up in culture, then washed with phosphate-buffered common salt solution (PBS) and incubated with 1.1ASML for 30 minutes at 40° C. As secondary antibody for the detection of the binding, there was used a rhodamine-coupled rabbit anti-mouse IgG and shown in the fluorescence microscope.

Construction of the cDNA expression banks and immunoscreening

PolyA+ RNA from BSp73ASMI cells was "primed" with oligo (dT) and hexanucleotides of different composition and synthesised with reverse transcriptase from AMV of the first strand of the cDNA. The second strand of the cDNA was produced with E. coli DNA polymerase I, RNaseH and E. coli ligase and subsequently the double-stranded cDNA linearised on the ends with T4DNA. The vectors pEX1, 2 and 3 (Stanley and Luzio, 1984), which make possible the fusioning of the cDNA in 3 different reading rasters, were cleaved with SmaI restriction endonuclease and ligated with the cDNA (T4 DNA ligase). Competent E. coli DH5 (pCI857) bacteria, which produce a temperature-sensitive repressor, are transfected with the pEX-cDNA constructants and cultured on nylon filters. The gene for the temperature-sensitive repressor RCIS57 lies on the plasmid pCI857, which is compatible with the pEX plasmids. At 28° C., the $1P_R$ promotor, which controls the synthesis of the fusion proteins, is inactivated. By temperature increase to 42° C., the CI repressor is inactivated and the synthesis of β-galactosidase/ASML fusion proteins massively set into action. The heat-induced bacteria colonies are subsequently denatured with chloroform vapour on the filters and these then incubated in PBS which contains 3% dry milk powder, lysozyme and DNase. The bacterial fusion proteins fixed on the nylon filter are now incubated with mAb1.1ASML and, after washing out of non-specifically-bound mAb, used for the detection of the binding as secondary antibody 125J-labelled rabbit anti-mouse IgG. After autoradiography, positive clones were isolated from the original bacteria filter and substantially analysed. One clone, which synthesised a fusion protein which reacted specifically with 1.1ASML, was pEX34. The pEX contained in the bacterial clone carries 167 nucleotide cDNA which, inter alia, codes for the epitope (or the antigen determinants), the specificity of which is carried by mAb1.1ASML.

The isolation of the total length cDNA mMeta-1 then took place according to standard methods.

Immunisation of the rats with mAb1.1ASML

BDX rats, which are syngenic to the BSp73 tumour cells, were injected subcutaneously or intraperitoneally with mAb1.1ASML (coupled to keyhole limpet haemocyananine), together with complete Freund's adjuvant. The first took place 10, 7 and 3 days before the injection of the BSpASML cells (into the fatty foot pad), the following then 3, 7, 11, 14 and 21 days thereafter. After 23 days, the rats were sacrificed, the various lymph nodes prepared and weighed and macroscopically visible lung metastases counted.

Figure 4:
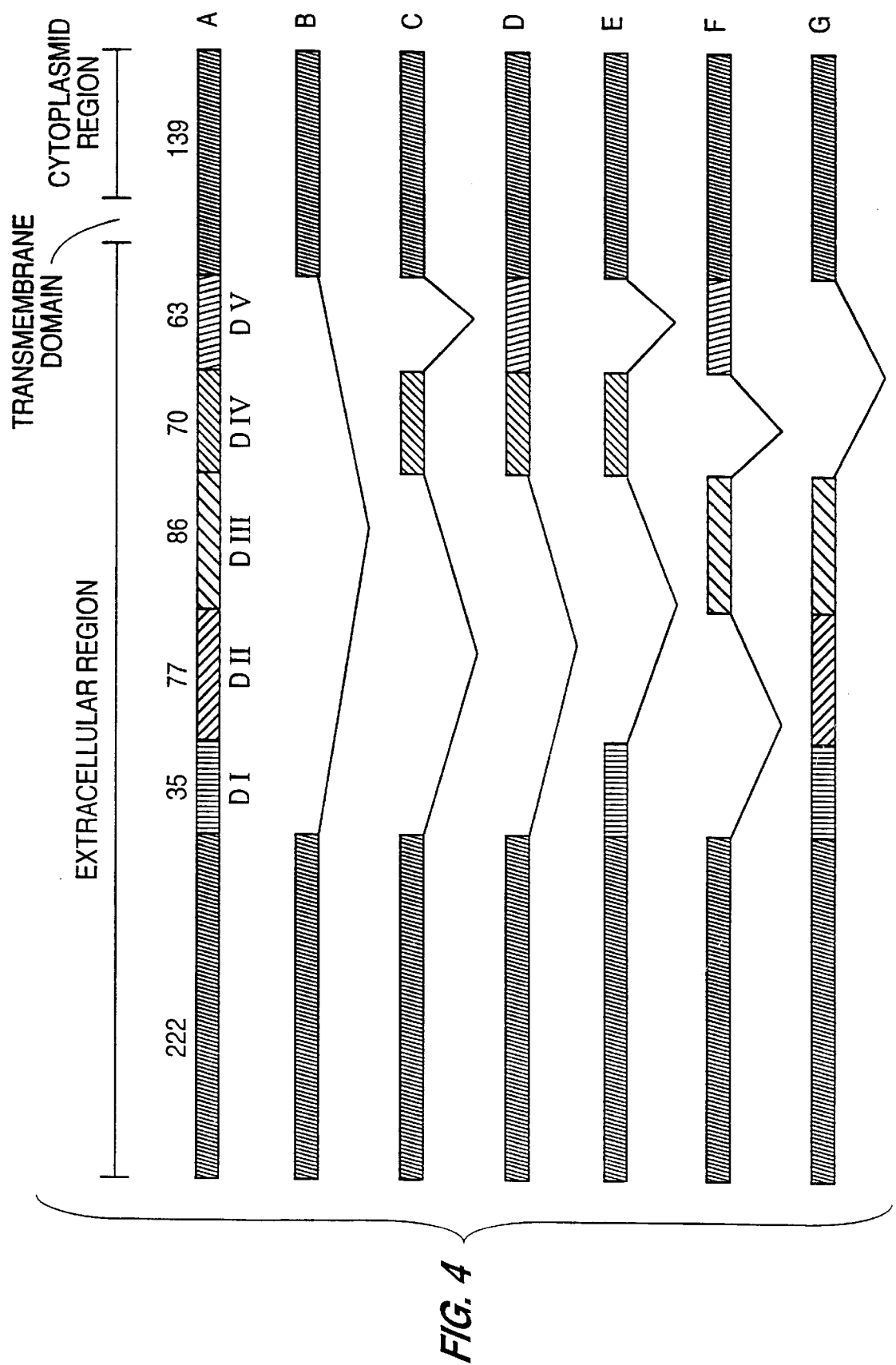
FIG. 4 depicts patterns of RNA derived from CD44.

Connection between the expression of variant CD44 surface proteins and metastatic potential In order to ascertain whether the expression of variant CD44 glucoproteins is merely a property of the investigated BSp73ASML cell line or whether the expression can be brought into connection with the metastatic potential, another series of rat tumour cells, which are derived from the 13762NF mammary carcinoma (Neri et al., 1982), were investigated. Furthermore, cell lines which were derived from the primary tumours (MTPa, MTC, MTF7 and MTA (group 1)) were compared with cell lines which are derived from lymph nodes and lung metastases (MTLy, MTLn2, MTLn3 (group 2)). The pattern of the RNA derived from CD44 is given in FIG. 4, whereby samples A, B and D correspond to the samples described on pages 5 and 6 of the Application, as well as to FIG. 1. Cells of group 1 all show a normal CD44 pattern with sample B. However, cells of group 2 show a pattern different therefrom. The RNA is larger than the RNA of group 1 and corresponds to the RNA of BSp73ASML. Smaller RNAs are lost in the case of the hybridisation with sample D. The other patterns show the similarity between the two rat tumour systems.

Also with the sample A, the RNA pattern of group 2 corresponds to that of BSp73ASML. Whereas sample A does not hybridise with RNA from BSp73AS, there is shown a small diffuse RNA band of about 2.5 kb in the case of cells of group 1. RNase and S1 protection analysis also show the structural similarity. From these results, an exchange in the cleavage pattern and the expression of variant CD44 RNAs appears to take place with the formation of metastases.

Transfer of the metastatic potential to non-metastasing BSp73AS cells by overexpression of pMeta-1

The connection of the expression of variant CD44 species with the metastatic potential in two series of rat tumours indicates a causal role of the glyco-proteins in the metastatic process. In order to investigate this, pMeta-1 was transferred into BSp73AS cells and investigated whether the behaviour of the cells is thereby changed. The complete coding region of the pMeta-1 FIGS. 2a–2h, SEQ ID NO:1 was inserted below the SV40 promotor and this formation (diagram in FIG. 5) introduced into the BSp73AS cells, together with PSV2neo. Individual G418-resistant and pMeta-1-expressing colonies were obtained. The RNA pattern of 2 of these colonies is shown in FIG. 5. The hybridisation of the variant CD44-specific sample A shows a dominant transcript of approximately 2.2 kb which corresponds to the size of the smallest frequent RNA which is transcribed in BSp73ASML cells (FIG. 5). However, the transfected cells contain about 10 times as much of this RNA as BSp73ASML.

Other size orders are observed in one of the transfected cells (BSp73AS-pSVMeta-1–14), which could be dependent upon the place of the plasmid integration. A pSV2neo simulation transfer clone (not shown) and the BSp73AS receiver cells contain no RNA which is complementary to sample A. In order to discover the endogenic normal CD44 transcriptions (without the extra domains of the pSVMeta-1) in the transfects, the filter was stripped and rehybridised with sample D. This part of the non-transferred 3' sequence is not contained in the expression clone (cf. FIG. 5). Sample D detects two main transcripts of 2.9 and 4.9 kb in the RNA of the two transfects (FIG. 5, right column), not only in the control BSp73AS but also in the non-illustrated BSp73ASpSVneo.

Approximate quantifications of the various agreeing hybridisations show that the transfects express approximately 5× as much of the variant CD44 RNAs, which are transcribed by the expression plasmid, as the endogenic gene transcripts.

The overexpressed cDNA is transferred into a protein. The two transfects, which are illustrated in FIG. 5, synthesise mAb1-immune-colourable proteins of the same apparent size, namely, a main product of 150 kDa and a weaker band at 100 kDa. Since the cDNA sequence codes a primary protein product of only 503 amino acids (corresponds to about 60,000 Dalton), all visible bands must represent modified forms. The 150 kDa band runs together with one of the modified forms of variant CD44 which is expressed in the metastasing cells BSp73ASML. BSp73AS or simulation-transferred BSp73ASpSVneo do not possess this protein. As in BSp73ASML cells, the epitope of the cells expressed by the transfects lies freely on the cell surface.

In order to demonstrate that the expression of variant CD44 suffices in order to impart a metastatic potential to BSp73AS cells, transfects were injected into syngenic BDX rats (spontaneous metastasis protocol). In earlier experiments, metastatic tumour cells BSp73ASML spread out quickly from the place of the injection and were completely distributed about 10 days after the injection (Matzku, 1984). All local tumours were, therefore, removed by amputations on the 10th day. All carriers of BSp73ASML cells and all animals which had been injected with an overexpressing transfect developed lung metastases (Table 1). The course of the metastasis formation was comparably quick within 5–8 weeks after the injection. Animals which had received Bsp73AS cells or simulation transfects were, after this time, completely healthy (apart from due to the amputation) and even after 5 months no metastases could be ascertained.

In spite of a surprising similarity in the strong metastasis formation, there are some interesting differences. In all animals, BSp73ASML cells reach the lymph nodes and lead to a massive enlargement of various nodes in the region of the inguinal groin and next to the aorta (Table 1). A transfect (BSp73AS-pSV meta-1–14) causes lymph node enlargement in 3 of 8 animals although all animals develop lung metastases (Table 1). No lymph node enlargement is ascertainable with the other transfect (BSp73AS-pSV Meta-1–15). The transfects appear, therefore, to be able to form colonies in the lungs without an obligatory growth phase of the lymph nodes.

The experiment according to Table 1 further points to another difference between BSp73AS transfects and BSp73ASML. The individual lung metastases are macroscopically visible, whereas those of BSp73ASML are small and numerous but, in a larger series with BSp73ASML (Reber et al., 1990), 11 of 20 animals develop 5–20 larger nodes per lung than the transfects.

In order to ascertain that the metastases formed were brought about by the injected transfects and in order to exclude the improbable possibility of a spontaneous mutation, which transfers a metastatic potential, the epitope-positive proteins in the total lung extracts and in the extracts of recultured metastasis-producing cells were determined. The 150 kDa glycoprotein is detectable in the whole lung extract, as well as in the extracts of a specific lung node from an animal which has received BSpAS-pSV meta-1–15 transfects. In the case of in vitro growth, the G418-resistant strain expresses a protein of the same apparent molecular weight.

Diagnosis and therapy

1. Analysis of human tumour material by in situ hybridisation with the human pMeta-1 sequence present. These experiments are considered as preliminary experiments before an Ab is available which recognises the human ECR.

2. Production of antibodies against the human ECR. Cloning of the human pMeta-1 sequences in bacterial expression vectors so that fusions arise with β-galactosidase or tryptophane E-product. Immunisation of rabbits with these fusion proteins or with synthesised peptides from the ECR (coupled to carrier molecules). Isolation of the polyvalent or monospecific antibodies.

Possibilities of use

Immunohistological investigations of clinical tumour material (diagnosis)

Detection of soluble ECR in the serum of patients with the help of ELISA tests (diagnosis)

Construction of toxin-coupled antibodies in order, with the help of the antibody, to bring the toxin into the tumour/metastasis region (therapy)

Construction of antibodies with two definite antigen binding positions. By means of this double specificity, the attempt is to be made to initiate cytotoxic reactions in the metastasis region (e.g. anti CD2 or CD3 coupling) (therapy).

3. Production of hMeta-1 protein by transfection of human or rat cells with an expression vector which carries the complete hMeta-1 cDNA sequence; or purification from LCLC97 cells.

Possibilities of use

Injection of the protein or parts thereof in order to block the tissue binding positions of the tumour cells After characterisation of the binding positions, a use for therapy would also be conceivable which could depend upon the injection of large amounts of binding protein which would then block the migrating tumour cells.

List of literature

Goldstein, L. A., Zhou, D. F., Picker, I. J., Minty, C. N., Bargatz, R. F., Ding, J. F. and Butcher, E. C. (1989), A human lymphocyte homing receptor, the hermes antigen, is related to cartilage proteoglycan core and link proteins, Cell 56: 1063–1072.

Hart, I. R., Goode, N. T. and Wilson, R. E. (1989), Molecular aspects of the metastatic cascade, Biochim. Biophys. Acta 989: 65–84.

Idzerda, R. L., Carter, W. G., Nottenburg, C., Wayner, E. A., Gallatin, W. M. and St. John, T. (1989), Isolation and DNA sequence of a cDNA clone encoding a lymphocyte adhesion receptor for high endothelium, Proc. Natl. Acad. Sci. U.S.A. 86: 4659–4663.

Köhler, G. (1981) In: I. Lefkovits and B. Pernis (eds), Immunological Methods, Vol. 2, p.285, N.Y. Academic Press.

Matzku, S., Komitowski, Mildenberger and Zoller, M. (1983), Caharacterization of Bsp 73, a spontaneous rat tumor and its in vivo selected variants showing different metastasizing capacities, Inv. Met. 3: 109–123.

Matzku, S., Wenzel, A., Liu, S. and Zoller, M. (1989), Antigenic differences between metastatic and non-metastatic BSp73 rat tumor variants characterized by monoclonal antibodies, Cancer Res. 49: 1294–1299.

Neri, A., Welch, D., Kawaguchi, T. and Nicolson, G. L. (1982), Development and biologic properties of malignant cell sublines and clones of spontaneously metastasizing rat mammary adenocarcinoma, J. Natl. Cancer Inst. 68: 507–517.

Nicolson, G. L. (1987), Tumor cell instability, diversification, and progression to the metastatic phenotype; from oncogene to oncofetal expression, Cancer Res. 47: 1473–1487.

Nottenburg, C., Rees, G. and St. John, T. (1989), Isolation of mouse CD44 cDNA: structural features are distinct from the primate cDNA, Proc. Natl. Acad. Sci. U.S.A. 86: 8521–8525.

Stamenkovic, I., Amiot, M., Pesando, J. M. and Seed, B. (1989), A lymphocyte molecule implicated in lymph node homing is a member of the cartilage link protein family, Cell 56: 1057–1062.

Stanley K. K. and Luzio, J. P. (1984), Construction of a new family of high efficiency bacterial expression vectors: identification of cDNA clones coding for human liver proteins, EMBO J. 3: 1429–1434.

Wenzel, A. (1986), Charakterisierung von Differenzierungsantigenen auf dem Rattentumor Bsp 73 mit Hilfe monoklonaler Antikörper (Characterisation of differentiation antigens on the rat tumour Bsp 73 with the help of monoclonal antibodies), Diploma Dissertation, University of Karlsruhe.

Zhou, D. F. H., Ding, J. F., Picker, L. F., Bargatze, R. F., Butcher, E. C. and Goeddel, D. V. (1989), Molecular cloning and expression of Pgp-1—The mouse homolog of the human H-CAM (Hermes) lymphocyte homing receptor, J. Immunol. 143: 3390–3395.

TABLE 1

Metastatic spreading out of BSp73AS cells which express variant CD44 cDNA pMeta-1***

| tumour clone | local appear-ance | *LN ing | distribution in the case of metastatic autopsy *LN par | lung |
|---|---|---|---|---|
| BSp73ASML | 0/8 | 8/8 ⌀ 1.5–2.5** | 8/8 ⌀ 2.5–5.0 | 8/8 miliary |
| BSp73AS-pSVMeta-1-14 | 0/8 | 3/8 ⌀ 0.3–1.2 | 3/8 ⌀ 1.0–4.5 | 8/8 multiple |
| BSp73AS-pSVMeta-1-15 | 0/8 | 0/8 | 0/8 | ⌀ 0.3–5.0 8/8 5–20 |
| BSp73AS | 1/8 | 0/8 | 0/8 | ⌀ 0.3–10.0 0/8 |
| BSp73AS-pSVneo | 0/8 | 0/8 | 0/8 | 0/8 |

**average diameter in mm
***the Table gives the stage 60 days after injection of the given cells
*LN = lymph nodes

What is claimed is:

1. An antibody that reacts with a variant epitope in the extracellular region of a variant CD44 polypeptide, said variant epitope encoded by a DNA fragment having the nucleotide sequence:

AAC CCA AGC CAT TCA AAT CCG

GAA GTG CTA CTT CAG ACA ACC ACA

AGG ATG ACT GAT GTA GAC AGA AAT

GGC ACC ACT GCT TAT GAA GGA AAC

TGG AAC CCA GAA GCA CAC CCT CCC

CTC ATT CAC CAT GAG CAT CAT GAG

GAA GAA GAG ACC CCA CAT TCT ACA

AGC ACA ATC CAG GCA ACT CCT AGT

AGT ACA ACG GAA GAA ACA GCT ACC

CAG AAG GAA CAG TGG TTT GGC AAC

AGA TGG CAT GAG GGA TAT CGC CAA

ACA CCC AGA GAA GAC TCC CAT TCG

ACA ACA GGG ACA GCT GCA GCC TCA

GCT CAT ACC AGC CAT CCA ATG CA (bases 229–560 of SEQ ID NO:3).

2. A composition comprising an antibody according to claim 1, wherein said antibody is polyclonal, and an acceptable carrier.

3. A composition comprising an antibody according to claim 1, wherein said antibody is monoclonal, and an acceptable carrier.

4. An agent comprising an antibody according to claim 1, coupled to a label.

5. An antibody that reacts with a variant epitope in the extracellular region of a variant CD44 polypeptide, said variant epitope having the amino acid sequence:

ISSTISTTPRAFDHTKQNQDWTQWNPSH-SNPEVLLQTTTR MTDVDRNGTTAYEGNWN-PEAHPPLIHHEHHEEEETPHSTS TIQATPSST-TEETATQKEQWFGNRWHEGYRQTPREDSHST TGTAAASAHTSHPMQGRTTPSPEDSSWT-DFFNPISHPMGR GHQAGRR (residues 53–219 of SEQ ID NO:4).

6. A composition comprising an antibody according to claim 5, wherein said antibody is polyclonal, and an acceptable carrier.

7. A composition comprising an antibody according to claim 5, wherein said antibody is monoclonal, and an acceptable carrier.

8. An agent comprising an antibody according to claim 5, coupled to a label.

9. The monoclonal antibody designated as mAb1.1 ASML produced by hybridoma, 1.1 ASML (Accession Number DSM ACC2363).

10. The hybridoma cell line, 1.1 ASML (Accession Number DSM ACC2363).

11. A method of identifying a variant epitope in the extracellular region of a variant CD44 polypeptide, comprising the steps of:
    contacting a sample suspected of containing said polypeptide with an antibody according to claim 1; and
    detecting said binding of said antibody to said polypeptide.

12. A method of identifying a variant epitope in the extracellular region of a variant CD44 polypeptide, comprising the steps of:
    contacting a sample suspected of containing said polypeptide with an antibody according to claim 5; and
    detecting said binding of said antibody to said polypeptide.

* * * * *